US012765807B2

(12) United States Patent
Sun et al.

(10) Patent No.: US 12,765,807 B2
(45) Date of Patent: Oct. 20, 2026

(54) NOVEL, ORGAN-ON-A-CHIP DEVICE FOR ASSESSING TRANS-EPITHELIAL TRANSPORT, AND USES THEREOF

(71) Applicant: The Johns Hopkins University, Baltimore, MD (US)

(72) Inventors: Sean X. Sun, Baltimore, MD (US); Mohammad Ikbal Choudhury, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1013 days.

(21) Appl. No.: 17/626,015

(22) PCT Filed: Jul. 8, 2020

(86) PCT No.: PCT/US2020/041163
§ 371 (c)(1),
(2) Date: Jan. 10, 2022

(87) PCT Pub. No.: WO2021/007300
PCT Pub. Date: Jan. 14, 2021

(65) Prior Publication Data

US 2022/0265176 A1 Aug. 25, 2022

Related U.S. Application Data

(60) Provisional application No. 62/871,464, filed on Jul. 8, 2019.

(51) Int. Cl.
*A61B 5/145* (2006.01)
*B01L 3/00* (2006.01)
(Continued)

(52) U.S. Cl.
CPC ........ *A61B 5/14507* (2013.01); *B01L 3/5027* (2013.01); *C12M 23/16* (2013.01);
(Continued)

(58) Field of Classification Search
CPC ............... A61B 5/14507; B01L 3/5027; B01L 2300/0681; B01L 2300/0861; B01L 3/502;
(Continued)

(56) References Cited

U.S. PATENT DOCUMENTS

2013/0230911 A1* 9/2013 Charest .................. B29C 59/00 435/297.1

OTHER PUBLICATIONS

Grantham et al., "In vitro fluid secretion by epithelium from polycystic kidneys", The Journal of Clinical Investigation, (1995), vol. 95, No. 1, pp. 195-202.

(Continued)

*Primary Examiner* — Abid A Mustansir
(74) *Attorney, Agent, or Firm* — Venable LLP; Ryan T. Ward

(57) ABSTRACT

Embodiments of the invention relate to devices and methods for measuring a fluidic flux and a fluidic pressure through a tissue layer. Related devices include: a first micro-patterned layer; a second micro-patterned layer attached to the first micro-patterned layer; a porous membrane disposed between the first micro-patterned layer and the second micro-patterned layer, where the second micro-patterned layer and the porous membrane together define an upper channel across an upper surface of the tissue layer while in use; where the first micro-patterned layer and the porous membrane together define a lower channel across a lower surface of the tissue layer while in use; and a pressure monitor arranged in operative communication with the upper and lower channels. The pressure monitor is configured to measure a fluidic pressure in the upper channel and a fluidic pressure in the lower channel.

12 Claims, 29 Drawing Sheets

(51) Int. Cl.
*C12M 1/12* (2006.01)
*C12M 3/06* (2006.01)

(52) U.S. Cl.
CPC ...... *C12M 25/02* (2013.01); *B01L 2300/0681* (2013.01); *B01L 2300/0861* (2013.01)

(58) Field of Classification Search
CPC ...... C12M 23/16; C12M 25/02; C12M 21/08; G01N 33/4833
See application file for complete search history.

(56) References Cited

OTHER PUBLICATIONS

Burg et al., "Control of fluid absorption in the renal proximal tubule", The Journal of Clinical Investigation, (1968), vol. 47, No. 9, pp. 2016-2024.
Dasgupta et al., "Physics of lumen growth", Proceedings of the National Academy of Sciences, (2018), vol. 115, No. 21, pp. E4751-E4757.
Heisenberg et al., "Forces in tissue morphogenesis and patterning", Cell, (2013), vol. 153, No. 5, pp. 948-962.
Miroshnikova et al., "Adhesion forces and cortical tension couple cell proliferation and differentiation to drive epidermal stratification", Nature cell biology, (2018), vol. 20, No. 1, p. 69.
Torres et al., "Mechanisms of disease: autosomal dominant and recessive polycystic kidney diseases", Nature Reviews Nephrology, (2006), vol. 2, No. 1, p. 40.
Lever, "Inducers of mammalian cell differentiation stimulate dome formation in a differentiated kidney epithelial cell line (MDCK)", Proceedings of the National Academy of Sciences, (1979), vol. 76, No. 3, pp. 1323-1327.
Latorre et al., "Active superelasticity in three-dimensional epithelia of controlled shape", Nature, (2018), vol. 563, No. 7730, p. 203.
Stroka et al., "Water permeation drives tumor cell migration in confined microenvironments", Cell, (2014), vol. 157, No. 3, pp. 611-623.
Li et al., "Flow-driven cell migration under external electric fields", Physical Review Letters, (2015), vol. 115, No. 26, p. 268101.
Kennedy et al., "Regulation of Na+, K+-ATPase activity in MDCK kidney epithelial cell cultures: Role of growth state, cyclic AMP, and chemical inducers of dome formation and differentiation", Journal of Cellular Physiology, (1984), vol. 121, No. 1, pp. 51-63.
Wilson, "Polycystic kidney disease", New England Journal of Medicine, (2004), vol. 350, No. 2, pp. 151-164.
Wang et al., "Vasopressin directly regulates cyst growth in polycystic kidney disease", Journal of the American Society of Nephrology, (2008), vol. 19, No. 1, pp. 102-108.
Grantham et al., "The importance of total kidney vol. in evaluating progression of polycystic kidney disease", Nature Reviews Nephrology, (2016), vol. 12, No. 11, p. 667.
Torres et al., "Tolvaptan in patients with autosomal dominant polycystic kidney disease", New England Journal of Medicine, (2012), vol. 367, No. 25, pp. 2407-2418.
Gattone et al., "Inhibition of renal cystic disease development and progression by a vasopressin V2 receptor antagonist", Nature Medicine, (2003), vol. 9, No. 10, p. 1323.
Gudipaty et al., "Mechanical stretch triggers rapid epithelial cell division through Piezo1", Nature, (2017), vol. 543, No. 7643, p. 118.
Yang et al., "A microscale pressure sensor based on immiscible fluid/fluid interface", Scientific Reports, (2019), vol. 9, (10 pages).
Maschmeyer et al., "A four-organ-chip for interconnected long-term co-culture of human intestine, liver, skin and kidney equivalents", Lab on a Chip, (2015), vol. 15, pp. 2688-2699.
Weinstein, "A mathematical model of rat proximal tubule and loop of Henle", American Journal of Physiology-Renal Physiology, (Feb. 18, 2015), vol. 308, pp. F1076-F1097.
Jiang et al. "Cellular pressure and volume regulation and implications for cell mechanics", Biophysical Journal, (Aug. 2013), vol. 105, pp. 609-619.
Grantham et al., "Volume progression in autosomal dominant polycystic kidney disease: the major factor determining clinical outcomes." Clinical Journal of the American Society of Nephrology, (20060, vol. 1, pp. 148-157.
Rohatgi et al., "Cyst fluid composition in human autosomal recessive polycystic kidney disease." Pediatric Nephrology, (2005), vol. 20, pp. 552-553.
Hopp et al., "Functional polycystin-1 dosage governs autosomal dominant polycystic kidney disease severity", The Journal of Clinical Investigation, (2012), vol. 122, No. 11, pp. 4257-4273.
Brasier et al., "Loss of the polycystic kidney disease (PKD1) region of chromosome 16p13 in renal cyst cells supports a loss-of-function model for cyst pathogenesis", The Journal of Clinical Investigation, (1997), vol. 99, No. 2, pp. 194-199.
Terryn et al., "Fluid transport and cystogenesis in autosomal dominant polycystic kidney disease", Biochimica et Biophysica Acta (BBA)-Molecular Basis of Disease, (2011), 1812.10, pp. 1314-1321.

* cited by examiner

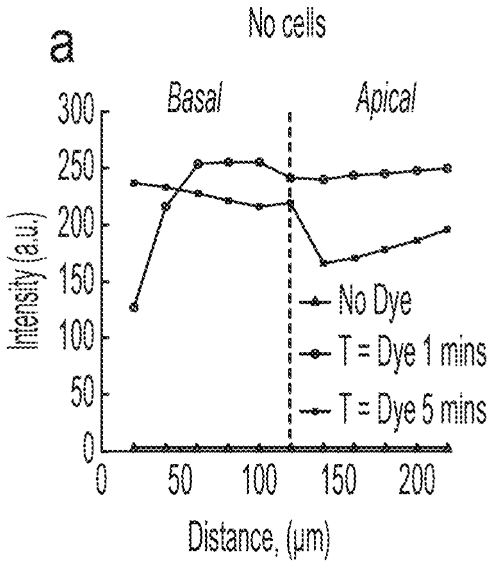
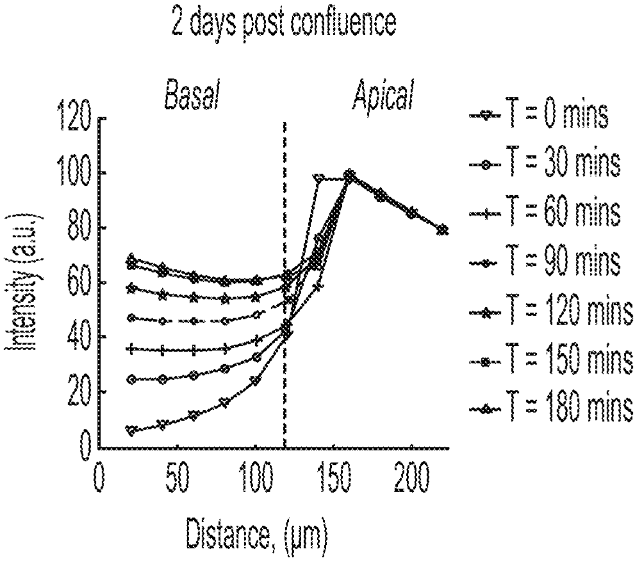
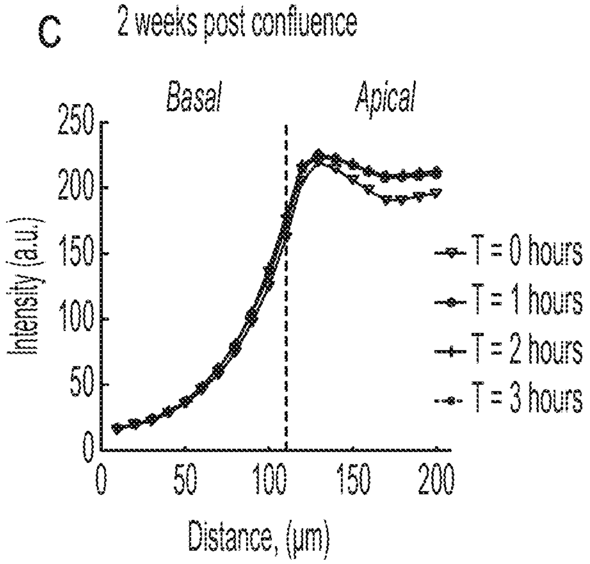
FIGS. 11A-11F

NOVEL, ORGAN-ON-A-CHIP DEVICE FOR ASSESSING TRANS-EPITHELIAL TRANSPORT, AND USES THEREOF

CROSS-REFERENCE TO RELATED APPLICATIONS

This application is a National Stage Application under 35 U.S.C. § 371 PCT/US2020/41163, filed Jul. 8, 2020, which claims priority to U.S. Provisional Application No. 62/871,464 filed Jul. 8, 2019; the entire contents of which are hereby incorporated by reference.

BACKGROUND

1. Technical Field

The field of the currently claimed embodiments of this invention relates to methods and devices for measuring a fluid flow and/or a fluidic pressure through a tissue layer.

2. Discussion of Related Art

Many organs are made of a series of tubules lined with epithelial cells. For the human kidney, roughly one million nephrons with 30 kilometers of epithelial tubules re-absorb 180 L of water per day [1]. While the absorption activity of renal epithelial cells has been studied both in vitro and in vivo [2-4], the influence of forces and hydraulic pressures during absorption has not been examined, mainly due to difficulty in controlling these variables during experimentation. Moreover, it is useful to study fluid absorption, secretion and transport across all types of epithelium, including but not limited to intestines, pancreas, lung, mammary gland, blood-brain-barrier and blood vessels.

Mechanical forces are recognized as important elements during cell growth, differentiation and tissue morphogenesis [5-7]. For kidney disorders such as the polycystic kidney disease (PKD), where tubular morphology of the epithelium becomes disrupted and uncontrolled expansion of the cyst eventually results, mutations in polycystins must also alter the mechanical state of the kidney epithelium [8]. Forces developed during fluid transport is a general phenomenon in all types of tissues, affecting development and disease progression.

There remains a need for a device and method that can be reliably and readily used to study and measure the ability of tissues to move fluid through the tissue layer.

INCORPORATION BY REFERENCE

All publications and patent applications identified herein are incorporated by reference in their entirety and to the same extent as if each individual publication or patent application was specifically and individually indicated to be incorporated by reference.

SUMMARY

An embodiment of the current invention relates to a microfluidic device for measuring a fluidic flux through a tissue layer, having a first micro-patterned layer; a second micro-patterned layer attached to the first micro-patterned layer; a porous membrane disposed between the first micro-patterned layer and the second micro-patterned layer, where the second micro-patterned layer and the porous membrane together define an upper channel across an upper surface of the tissue layer while in use; where the first micro-patterned layer and the porous membrane together define a lower channel across a lower surface of the tissue layer while in use; and a pressure monitor arranged in operative communication with the upper and lower channels. In such an embodiment, the pressure monitor is configured to measure a fluidic pressure in the upper channel and a fluidic pressure in the lower channel to provide a measurement of the fluidic flux.

An embodiment of the current invention relates to a method for measuring a fluidic flux through a tissue layer, including: growing the tissue layer on a porous membrane such that the tissue layer has an upper surface on a side away from the porous membrane and a lower surface in contact with and spanning pores of the porous membrane; flowing a fluid across and in fluid contact with the upper surface of the tissue layer; and measuring fluidic flux from at least one of the lower surface and the upper surface of the tissue layer to provide a measure of the fluidic flux through the tissue layer. In such an embodiment, the tissue layer is a continuous layer without gaps such that portions of the fluid flowed across the upper surface of the tissue layer only pass through the porous membrane by passing through cells of the tissue layer.

An embodiment of the invention relates to a method for assaying an agent's impact on fluidic flux across a tissue layer, including: growing the tissue layer on a porous membrane, such that the tissue layer has an upper surface on a side away from the porous membrane and a lower surface in contact with and spanning pores of the porous membrane; flowing a fluid comprising the agent across and in fluid contact with at least one of the lower surface and the upper surface of the tissue layer; measuring fluid flux from at least one of the lower surface and the upper surface of the tissue layer to provide a measure of the fluidic flux through the tissue layer; and comparing the fluidic flux to a control fluidic flux level, wherein a change in the fluidic flux as compared to the control fluidic flux level is indicative that the agent impacts fluidic flux across the tissue layer. In such an embodiment, the tissue layer is a continuous layer without gaps such that portions of the fluid flowed across at least one of the lower surface and the upper surface of the tissue layer only pass through the porous membrane by passing through cells of the tissue layer.

An embodiment of the invention relates to a system for measuring a fluidic flux across a tissue layer and fluidic pressure including a microfluidic device, the microfluidic device including: a first micro-patterned layer; a second micro-patterned layer attached to the first micro-patterned layer; a porous membrane disposed between the first micro-patterned layer and the second micro-patterned layer, wherein the second micro-patterned layer and the porous membrane together define an upper channel across an upper surface of the tissue layer while in use; wherein the first micro-patterned layer and the porous membrane together define a lower channel across a lower surface of the tissue layer while in use; and a pressure monitor arranged in operative communication with the upper and lower channels. In such an embodiment, the pressure monitor is configured to measure a fluidic pressure in the upper channel and a fluidic pressure in the lower channel to provide a measurement of the fluidic flux.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

In embodiments described throughout, the terms "upper channel" and "lower channel" are relative terms that more broadly relate to the location of a channel with respect to the orientation of a tissue layer. An "upper channel" refers to a channel located on an apical side of the tissue layer, while a "lower channel" refers to a channel located proximal to the basal side of the tissue layer.

In embodiments described throughout, the terms "fluidic flux" and "flux" are used interchangeably and generally relate to a movement of fluid and/or molecules across a barrier. In some embodiments, a molecular flux is an example of a fluidic flux. In some embodiments, the barrier is a tissue layer and/or a porous membrane. In some embodiments, the fluidic flux is measured as a function of fluidic pressure across the barrier. In some embodiments, the fluidic flux is measured as a function of a difference in fluidic pressure between a fluidic pressure on a basal side of a tissue layer, and a fluidic pressure on an apical side of the tissue layer and/or as a function of a difference in fluidic pressure between a fluidic pressure in a lower channel of a device, and a fluidic pressure on an upper channel of the device.

Figure 1A:
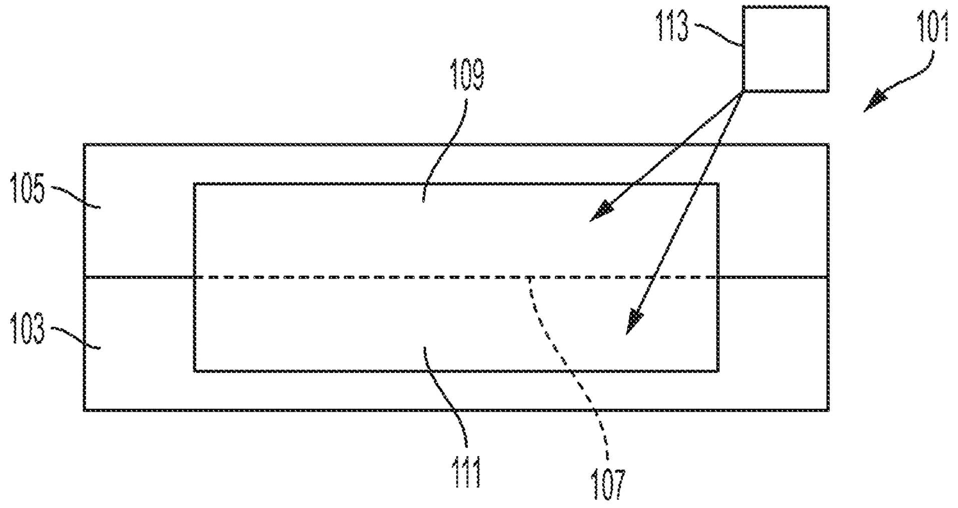
FIGS. 1A and 1B are schematic illustrations of microfluidic devices for measuring a fluidic flux through a tissue layer according to embodiments of the invention.
Figure 1B:
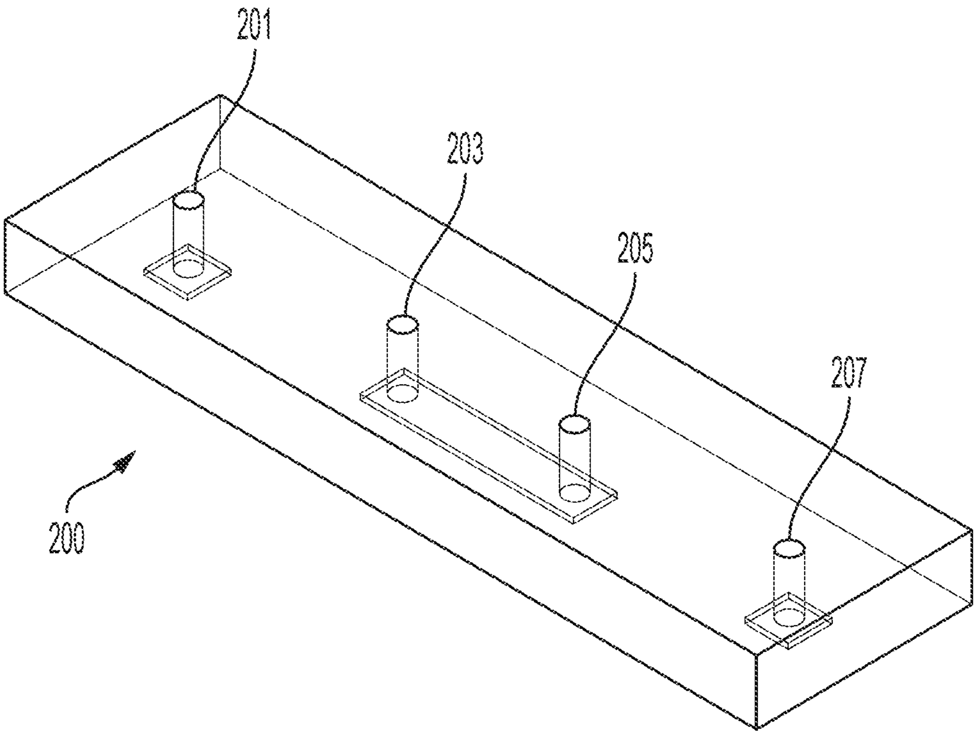

FIG. 1A is an illustration of a cross-sectional view of a microfluidic device 101 for measuring a fluidic flux through a tissue layer according to an embodiment of the invention. In FIG. 1A, the microfluidic device includes a first micro-patterned layer 103; a second micro-patterned layer 105 attached to the first micro-patterned layer 103; a porous membrane 107 disposed between the first micro-patterned layer 103 and the second micro-patterned layer 105, where the second micro-patterned layer 105 and the porous membrane 107 together define an upper channel 109 across an upper surface of the tissue layer while in use; where the first micro-patterned layer 103 and the porous membrane 107 together define a lower channel 111 across a lower surface of the tissue layer while in use; and a pressure monitor and/or fluidic flux monitor 113 arranged in operative communication with the upper and/or lower channels. In such an embodiment, the pressure monitor 113 is configured to measure a fluidic pressure in the upper channel and/or a fluidic pressure in the lower channel; the fluidic flux monitor 113 arranged in operative communication with the upper and/or lower channels. In such an embodiment, the fluidic flux monitor is configured to measure a fluidic flux in the upper channel and/or a fluidic flux in the lower channel and is also configured to provide a measurement of the fluidic flux. Both the pressure monitor and fluid flux monitor can, but not necessarily, use the same measurement setup. The pressure monitor and fluidic flux monitor can be a single unit, or separate units. FIG. 1B is an illustration, in perspective view, of an embodiment of a second micro-patterned layer 200 defining four ports 201, 203, 205 and 207. In FIG. 1B, each of the four ports 201, 203, 205 and 207 allow access to one or more of the upper channel and the lower channel.

The first micro-patterned layer 103 and second micro-patterned layer 105 can each be, or include, a structure formed by spin-coating a polymer, such as, but not limited to, PDMS onto a micro patterned template. The micro patterned template can be a substrate that has micro-imprinted structures on it. For example, the micro patterned template can be a silicon wafer that has micro-imprinted structures produced by photolithography. However, the broad concepts of the current invention are not limited to only this example. The first micro-patterned layer 103 and second micro-patterned layer 105 can each be made from off-the-shelf items, such as, but not limited to, single- or double-sided tapes. In some embodiments, the said micro-patterns can be punched manually or automatically using a pre-designed punch or cutting tool.

By way of non-limiting example, the porous membrane 107 can be made of, or can include, a rigid or flexible material. Non-limiting example materials the porous membrane can be made of or include are PDMS, polycarbonate, polyethylene terephthalate, polytetrafluoroethylene, etc. The porous membrane 107 can also include synthetic, natural, or naturally derived polymers, compounds and/or other materials, agents or compositions to enhance its biocompatibility and promote cell culture and/or tissue growth on either side of the porous membrane. The porous membrane can include pores of uniform or varied dimensions. The pores are not limited to a preferred diameter, but are small enough to prevent a predetermined cell from passing through.

The pressure monitor 113 can be, but is not limited to, one or more micro-capillaries. The pressure monitor 113 can also include an optical detection system (e.g. a camera, laser, etc.) to monitor the one or more micro-capillaries. Non-limiting examples of pressure monitors can include fluid height measurement embodiments (e.g. ruler, scale, etc). The pressure monitor 113 can also include an electrical detection system (e.g. capacitance, resistance, etc.) to monitor the one or more micro-capillaries. The pressure monitor 113 can also include a mechanical detection system (e.g. a fluidic pressure transducer, etc.) to monitor the fluidic pressure in the upper or the lower channels.

In embodiments described throughout, a first micro-patterned layer and/or a second micro-patterned layer are configured to allow for laminar flow of a fluid.

In embodiments described throughout, a porous membrane can be of any size, shape, or composition suitable to allow for the growth of cells. Also, average pore size can be of any size so long as the pores are small enough to prevent a cell of interest from passing through.

An embodiment of the current invention relates to a microfluidic device for measuring a fluidic flux and/or a fluidic pressure through a tissue layer, having a first micro-patterned layer; a second micro-patterned layer attached to the first micro-patterned layer; a porous membrane disposed between the first micro-patterned layer and the second micro-patterned layer, where the second micro-patterned layer and the porous membrane together define an upper channel across an upper surface of the tissue layer while in use; where the first micro-patterned layer and the porous membrane together define a lower channel across a lower surface of the tissue layer while in use; and a pressure monitor arranged in operative communication with the upper and lower channels. In such an embodiment, the pressure flux is configured to measure a fluidic pressure in the upper channel and a fluidic flux in the lower channel to provide a measurement of the fluidic flux.

An embodiment of the current invention relates to a microfluidic device for measuring a fluidic flux through a tissue layer, having a first micro-patterned layer; a second micro-patterned layer attached to the first micro-patterned layer; a porous membrane disposed between the first micro-patterned layer and the second micro-patterned layer, where the second micro-patterned layer and the porous membrane together define an upper channel across an upper surface of the tissue layer while in use; where the first micro-patterned layer and the porous membrane together define a lower channel across a lower surface of the tissue layer while in use; and a pressure monitor arranged in operative communication with the upper and lower channels. In such an embodiment, the pressure flux is configured to measure a fluidic pressure in the upper channel and a fluidic flux in the lower channel to provide a measurement of the fluidic flux.

An embodiment of the invention relates to the device above, where at least one of the first and second micro-patterned layers further includes a base layer attached to at least one of the first and second micro-patterned layers.

An embodiment of the invention relates to the device above, where the porous membrane has a thickness of up to 50 micrometers.

An embodiment of the invention relates to the device above, where the porous membrane comprises a plurality of pores that have sizes sufficiently small such that cells within the tissue layer will not pass therethrough.

An embodiment of the invention relates to the device above, where the porous membrane comprises a plurality of pores that have an ensemble average diameter of between about 1 micrometer to about 10 micrometers.

An embodiment of the invention relates to the device above, further comprising an extracellular matrix protein coating on at least one side of the porous membrane.

An embodiment of the invention relates to the device above, where the upper and lower channels are each sufficiently narrow in a cross-sectional dimension such that the upper channel and the lower channel each support laminar flow.

An embodiment of the current invention relates to a method for measuring a fluidic flux and/or a fluidic pressure through a tissue layer, including: growing the tissue layer on a porous membrane such that the tissue layer has an upper surface on a side away from the porous membrane and a lower surface in contact with and spanning pores of the porous membrane; flowing a fluid across and in fluid contact with the upper surface of the tissue layer; and measuring fluidic flux and/or a fluidic pressure from at least one of the lower surface and the upper surface of the tissue layer to provide a measure of the fluidic flux and/or the fluidic pressure through the tissue layer. In such an embodiment, the tissue layer is a continuous layer without gaps such that portions of the fluid flowed across the upper surface of the tissue layer only pass through the porous membrane by passing through cells of the tissue layer.

An embodiment of the current invention relates to a method for measuring a fluidic flux through a tissue layer, including: growing the tissue layer on a porous membrane such that the tissue layer has an upper surface on a side away from the porous membrane and a lower surface in contact with and spanning pores of the porous membrane; flowing a fluid across and in fluid contact with the upper surface of the tissue layer; and measuring fluidic flux from at least one of the lower surface and the upper surface of the tissue layer to provide a measure of the fluidic flux through the tissue layer. In such an embodiment, the tissue layer is a continuous layer without gaps such that portions of the fluid flowed across the upper surface of the tissue layer only pass through the porous membrane by passing through cells of the tissue layer.

An embodiment of the invention relates to the method above, where a fluidic flux monitor in operative communication with at least one of the upper surface and the lower surface of the tissue layer is configured to measure fluidic flux.

An embodiment of the invention relates to the method above, where the fluidic flux monitor comprises a sufficiently narrow channel employing one or more of optical, electrical, and mechanical transducers. The fluidic flux monitor can be, but is not limited to, one or more micro-capillaries. The fluidic flux monitor can also include an optical detection system (e.g. a camera, laser, etc.) to monitor the said narrow channels. Non-limiting examples of fluidic flux monitor can include fluid height measurement embodiment (e.g. ruler, scale, etc.). The fluidic flux monitor can also include an electric detection system (e.g. capacitance, resistance, etc.) to monitor the one or more micro-capillaries. The fluidic flux monitor can also include an mechanical detection system (e.g. a fluidic flux transducer, etc.) to monitor the fluidic flux in the upper or the lower channels An embodiment of the invention relates to the method above, where the tissue layer is a substantially mono-cellular tissue layer substantially free of any intercellular gaps.

An embodiment of the invention relates to a method for assaying an agent's impact on fluidic flux and/or a fluidic pressure across a tissue layer, including: growing the tissue layer on a porous membrane, such that the tissue layer has an upper surface on a side away from the porous membrane and a lower surface in contact with and spanning pores of the porous membrane; flowing a fluid comprising the agent across and in fluid contact with at least one of the lower surface and the upper surface of the tissue layer; measuring fluid flux and/or fluidic pressure from at least one of the lower surface and upper surface of the tissue layer to provide a measure of the fluidic flux and/or of the fluidic pressure through the tissue layer; and comparing the fluidic flux and/or the fluidic pressure to a control fluidic flux level and/or to a control fluidic pressure level, wherein a change in the fluidic flux and/or in the fluidic pressure as compared to the control fluidic flux level and/or to the control fluidic pressure level is indicative that the agent impacts fluidic flux and/or fluidic pressure across the tissue layer. In such an embodiment, the tissue layer is a continuous layer without gaps such that portions of the fluid flowed across the upper surface of the tissue layer only pass through the porous membrane by passing through cells of the tissue layer.

An embodiment of the invention relates to a method for assaying an agent's impact on fluidic flux across a tissue layer, including: growing the tissue layer on a porous membrane, such that the tissue layer has an upper surface on a side away from the porous membrane and a lower surface in contact with and spanning pores of the porous membrane; flowing a fluid comprising the agent across and in fluid contact with at least one of the lower surface and the upper surface of the tissue layer; measuring fluid flux from at least one of the lower surface and upper surface of the tissue layer to provide a measure of the fluidic flux through the tissue layer; and comparing the fluidic flux to a control fluidic flux level, wherein a change in the fluidic flux as compared to the control fluidic flux level is indicative that the agent impacts fluidic flux across the tissue layer. In such an embodiment, the tissue layer is a continuous layer without gaps such that portions of the fluid flowed across the upper surface of the tissue layer only pass through the porous membrane by passing through cells of the tissue layer.

An embodiment of the invention relates to the method above, where the tissue layer is a substantially mono-cellular tissue layer substantially free of any intercellular gaps.

An embodiment of the invention relates to a system for measuring a fluidic flux and/or a fluidic pressure across a tissue layer comprising a microfluidic device, the microfluidic device including: a first micro-patterned layer; a second micro-patterned layer attached to the first micro-patterned layer; a porous membrane disposed between the first micro-patterned layer and the second micro-patterned layer, wherein the second micro-patterned layer and the porous membrane together define an upper channel across an upper surface of the tissue layer while in use; wherein the first micro-patterned layer and the porous membrane together define a lower channel across a lower surface of the tissue layer while in use; and a pressure monitor arranged in operative communication with the upper and lower channels. In such an embodiment, the pressure monitor is configured to measure a fluidic pressure in the upper channel and a fluidic pressure in the lower channel to provide a measurement of the fluidic flux.

An embodiment of the invention relates to a system for measuring a fluidic flux across a tissue layer comprising a microfluidic device, the microfluidic device including: a first micro-patterned layer; a second micro-patterned layer attached to the first micro-patterned layer; a porous membrane disposed between the first micro-patterned layer and the second micro-patterned layer, wherein the second micro-patterned layer and the porous membrane together define an upper channel across an upper surface of the tissue layer while in use; wherein the first micro-patterned layer and the porous membrane together define a lower channel across a lower surface of the tissue layer while in use; and a pressure monitor arranged in operative communication with the upper and lower channels. In such an embodiment, the pressure monitor is configured to measure a fluidic pressure in the upper channel and a fluidic pressure in the lower channel to provide a measurement of the fluidic flux.

An embodiment of the invention relates to the system above, further including a fluidic flux monitor in operative communication with at least one of the upper channel and the lower channel is configured to measure fluidic flux from at least one of the lower surface or the upper surface of the tissue layer to provide a measure of the fluidic flux through the tissue layer, and where the tissue layer is a continuous layer without gaps such that portions of a fluid flowed across the upper surface of the tissue layer only pass through the porous membrane by passing through cells of the tissue layer.

EXAMPLES

The following describes some concepts of the current invention with reference to particular embodiments. The general concepts of the current invention are not limited to the examples described.

An example embodiment is related to the design and development of a microfluidic organ-on-a-chip device to measure the trans-epithelial transport activity. The device is capable of measuring molecular flux across the epithelium as well as the pressure of fluid across monolayer of cells. The device comprises of a polydimethylsiloxane (PDMS) block with specific features, a polycarbonate porous membrane of 1 μm pore size, a patterned intermediate layer, a flat transparent base and a micro-capillary.

Example 1

The device has a plurality of compartments to simulate physiologically relevant condition. The micro-capillary serves one or more purposes along with the purpose of measuring flux and/or pressure in one or more than one compartment of the device. The device is fabricated with a plurality of porous membranes of various kinds. The cells can be plated on both sides of the membrane. The device has novel design strategies that enable measurement of fluid flux across a monolayer with sub-microliter resolution and fluid pressure alongside. The device is compatible with microscopy and can be used in experiments with a plurality of physiologically relevant mechanical, chemical, osmotic and hydraulic conditions.

This microfluidic organ-on-a-chip device is comprised of: (i) a patterned polydimethylsiloxane (PDMS) block; (ii) a porous membrane; (iii) separate apical and basal fluidic chambers; (iv) a micro-capillary; and (v) a flat transparent base.

The microfluidic organ-on-a-chip device comprises of a patterned PDMS block that houses one or more compartments in the device. The bottom part of the PDMS block is adhered to a fabricated bottom chamber, which has one or more patterns. The porous membrane is sandwiched between the PDMS and the bottom chamber. The free end of the chamber is glued to flat transparent base is made up of one or more materials such as glass, polymer, etc.

One or more micro-capillaries are attached to one or more compartments embodied in the microfluidic organ-on-a-chip device.

The microfluidic organ-on-a-chip device is low-cost, compatible with microscopy and can be used in experiments with a plurality of physiologically relevant mechanical, chemical and osmotic conditions.

Example 2

Using a novel microfluidic platform to recapitulate fluid absorption activity of kidney cells, it is demonstrated that renal epithelial cells can actively generate hydraulic pressure gradients across the epithelium. The fluidic flux declines with increasing hydraulic pressure until a stall pressure, at which the fluidic flux vanishes—in a manner similar to mechanical fluidic pumps. The developed pressure gradient translates to a force of 50-100 nanoNewtons per cell. For normal human kidney cells, the fluidic flux is from apical to basal, and the pressure is higher on the basal side. For human polycystic kidney disease (PKD) cells, the fluidic flux is reversed from basal to apical with a significantly higher stall pressure. Molecular studies and proteomic analysis reveal that renal epithelial cells are highly sensitive to hydraulic pressure gradients, developing different expression profiles and spatial arrangements of ion exchangers and the cytoskeleton in different pressure conditions. These results, together with data from osmotic and pharmacological perturbations of fluidic pumping, implicate mechanical force and hydraulic pressure as important variables during morphological changes in epithelial tubules, and provide further insights into pathophysiological mechanisms underlying the development of high luminal pressure within renal cysts.

Figures 2A, 2B, 2C, 2D, 2E, 2F, 2G, 2H, 2I, 2J:
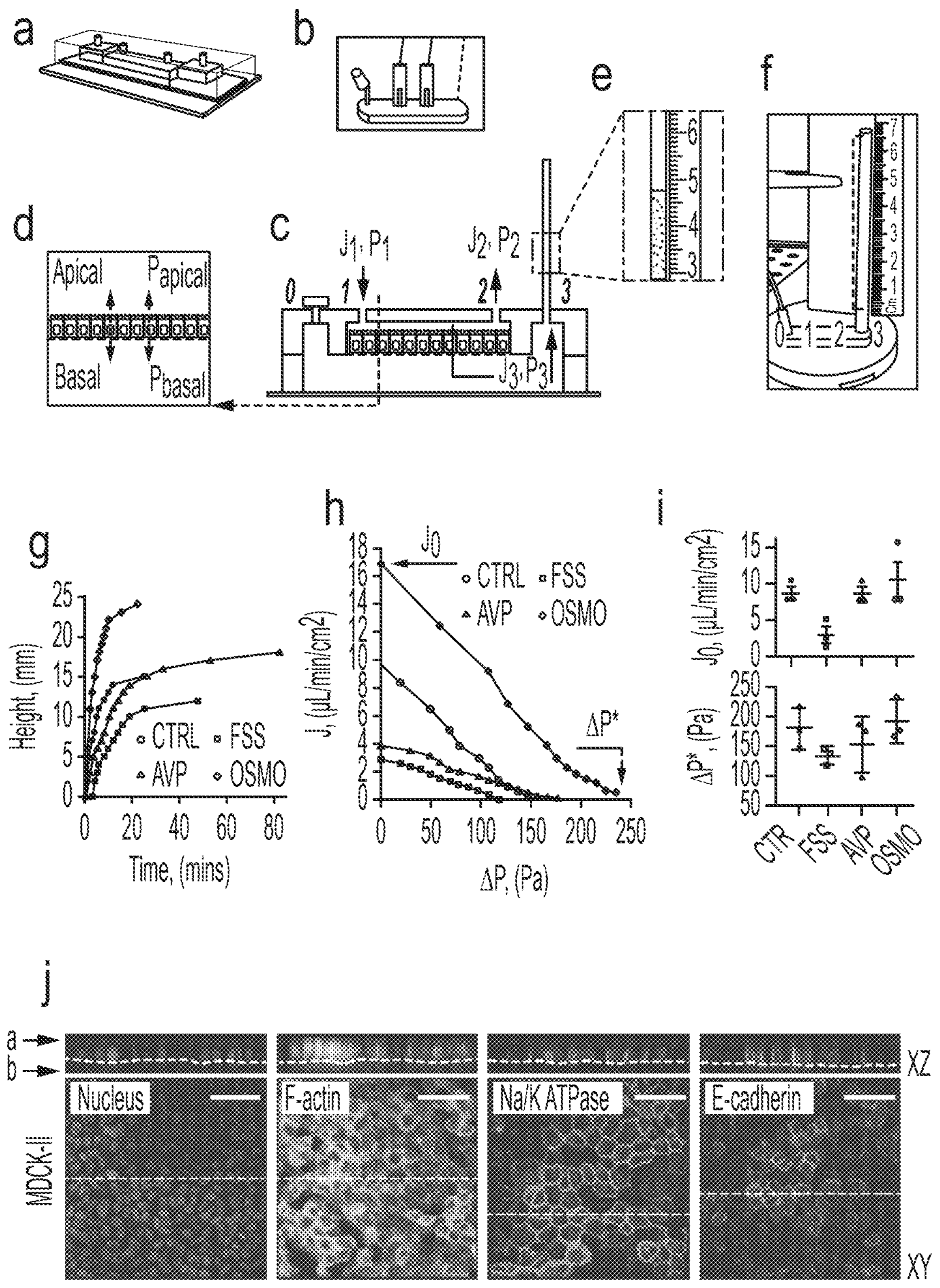
FIGS. 2A-2J are images of a microfluidic device for measuring a fluidic flux through a tissue layer according to an embodiment of the invention and graphs showing fluid pumping performance of cells seeded in it.

A micro-fluidic device to measure transepithelial fluid absorption activities of the kidney epithelium while allowing for cell imaging and simultaneous control of fluid pressure, shear stress (FSS), and media chemical composition is described herein (see FIG. 2A-2F). The device measures fluidic flux across the epithelium as a function of apical and basal pressures using a microcapillary (MC) connected to port 2 or 3 (FIG. 2C). The MC measures both the trans-epithelial fluid flux and the hydraulic pressure (FIG. 2C, 2F). It has a volume resolution of 0.31 μL and can detect pressure changes of 10 Pa. Calibration experiments are performed to obtain capillary action contribution from the MC to the basal pressure and the static pressure profiles of each device for the shear flow condition considered. Flow and pressure profiles of the entire device were also validated by simulation using FEM software.

When MDCK-II cells were seeded in the apical channel of the microfluidic device, cells settled on the porous membrane pre-treated with fibronectin and grew to confluence in 2-3 days. Upon further maturation, the epithelium showed classical cuboidal columnar morphology and formed a strong barrier, as tested using a dye permeation assay (see FIG. 11A-11F). Visualization using immunofluorescence (IF) showed that F-actin, Na/K ATPase and E-cadherin were localized in typical fashion (FIG. 2J). Mature MDCK-II epithelium developed apical to basal fluid flow, which can be visualized as a rise in fluid height in the MC beyond the static equilibrium height (FIG. 2G). The trans-epithelial fluid flux (J) from the apical to the basal channel depended on the hydrostatic pressure gradient ($\Delta P = P_{basal} - P_{apical}$) across the epithelium. J is maximal when $\Delta P = 0$ (denoted as J0), and declined until a stall pressure (static head) of $\Delta P^* \sim 100$-250 Pa was reached (FIG. **2*h*). This flux vs pressure curve resembled the classic pump performance curve (PPC) of mechanical fluid pumps. In contrast, for a passive filter, the pressure needs to be higher on the apical side to generate apical-basal flow, and the flux is zero when apical and basal pressures are equal. Therefore, kidney cells are active fluid pumps and the device can be considered as a microfluidic kidney pump (MFKP). The developed mechanical force is 30-100 nanoNewtons per cell, and constitutes a novel force generation mechanism that is perpendicular to the epithelium. This mechanism may be a general phenomenon for absorptive or secretory epithelia that perform fluid transport. Moreover, it was determined that PPC changes substantially under mechanical (FSS), chemical (addition of arginine vasopressin (AVP)) and hypo-osmotic gradient (OSMO) perturbations (FIG. 2**I), indicating active regulation by cells.

Figures 12A, 12Q:
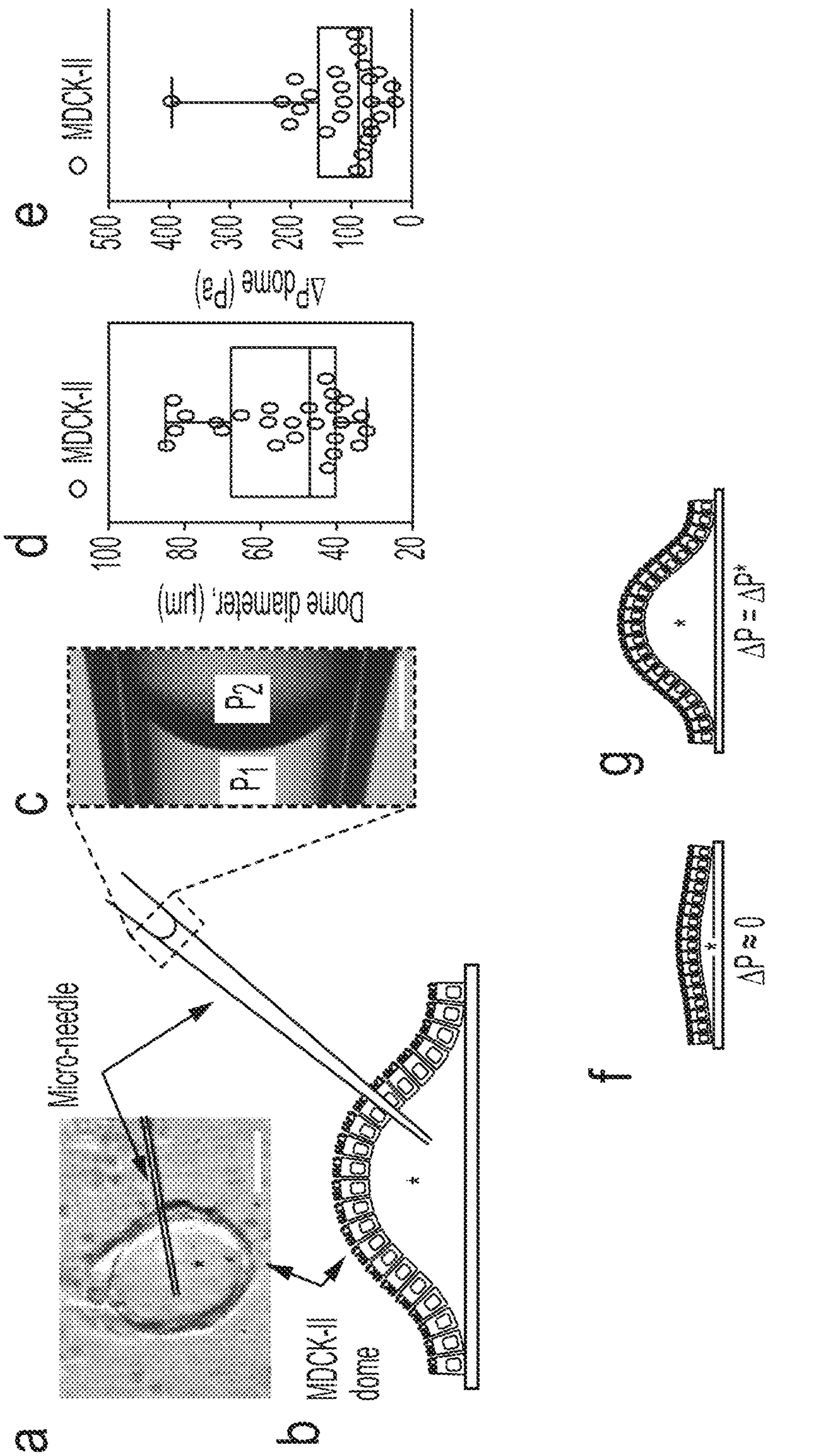
FIGS. 12A-12Q are images and graphs showing that MDCK-II domes exhibit similar trans-epithelial hydrostatic pressure gradient.
Figures 12A, 12Q:
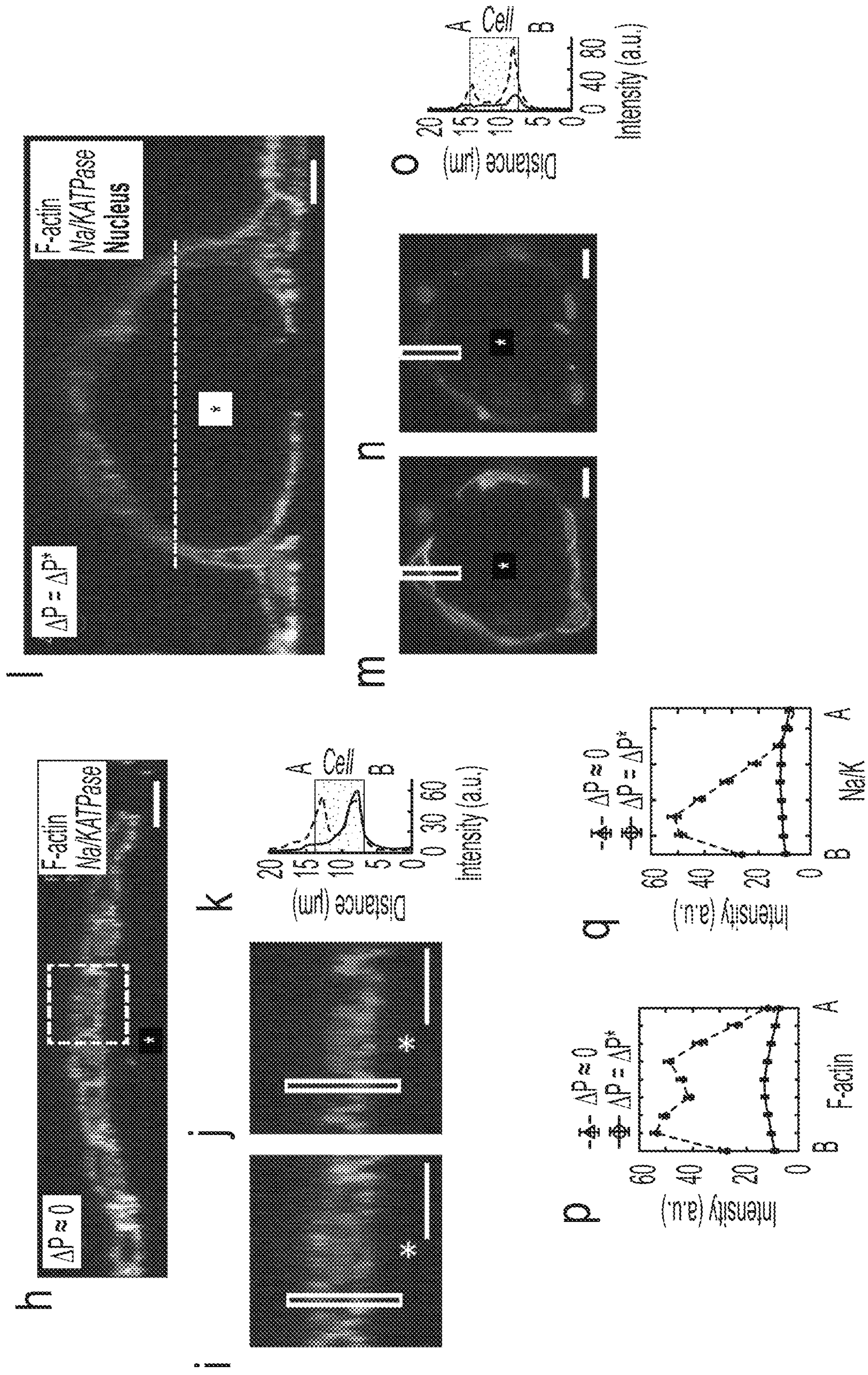
Figures 14A, 14B, 14C, 14D, 14E, 14F:
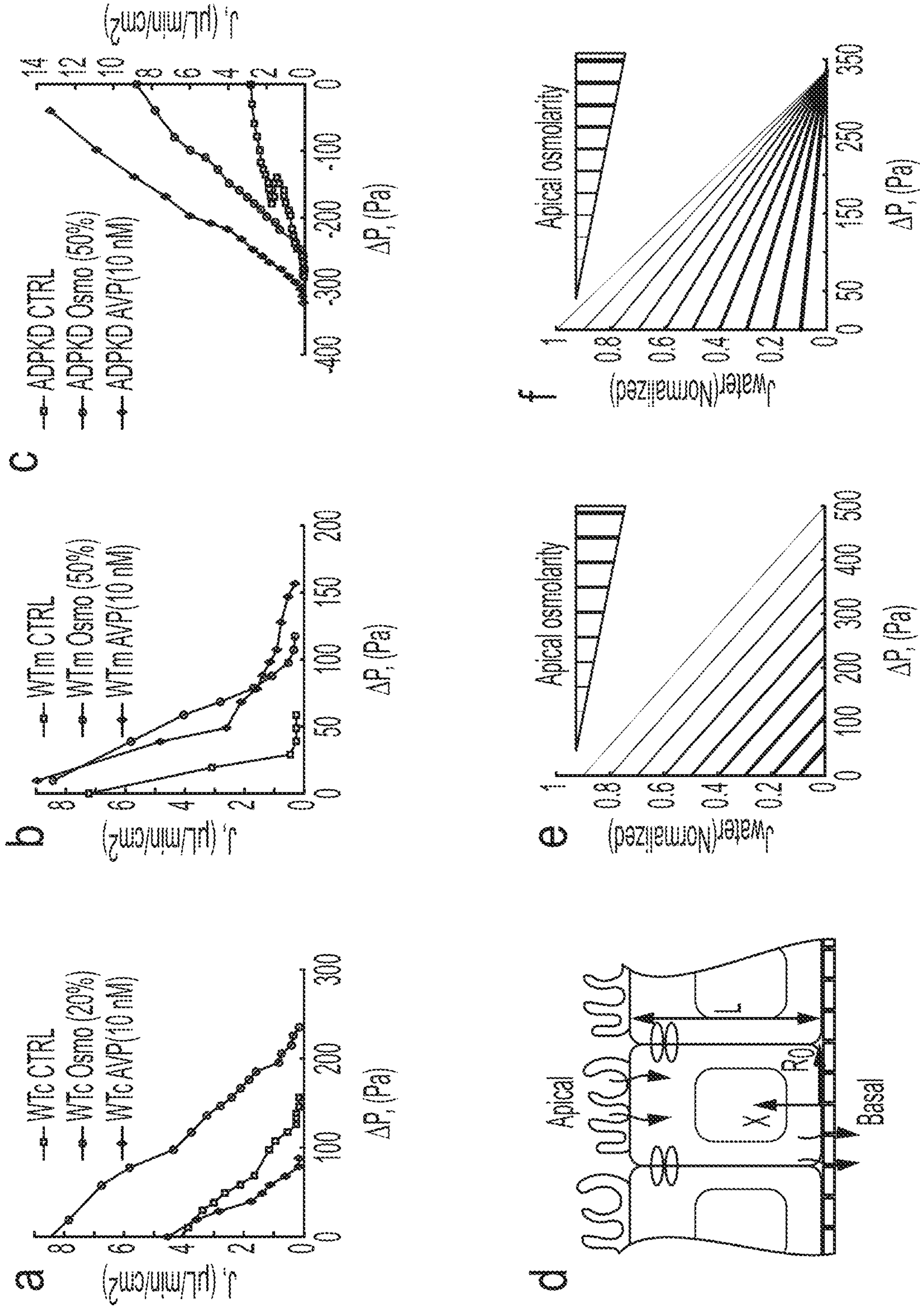
FIGS. 14A-14F are graphs showing that fluid pumping performance curves for various cell lines are dependent on mechanical, chemical and osmotic perturbations.

To validate the trans-epithelial pressure gradient measured from the device, a mature polarized MDCK-II monolayer on 2D impermeable substrates (glass), which formed dynamic fluid-filled domes with elevated internal hydrostatic pressure [9] was examined. This pressure was measured by inserting a glass micro-needle into MDCK-II domes while monitoring the curvature of an oil-media interface in the needle (FIG. 12A-12C). The dome hydraulic pressure is determined to be in the same range as measured in the MFKP (FIG. 12D, 12E), although in domes it was not possible to simultaneously monitor the trans-epithelial fluid flux. This result, together with traction force measurements of dome pressure [10], show that MDCK-II epithelium is capable of developing hydrostatic pressure of the order of 200 Pa by actively pumping fluid. To further understand the PPC curve, a mathematical model of the PPC based on active transport of an idealized solute ([11,12]) was developed. If the active flux for the ideal solute depends linearly on the osmotic pressure difference across the cell apical and basal surface, then the model predicts a similar PPC that shifts with changes in apical hypo-osmotic gradient, as observed in experiments (FIG. 14D, 14E).

The device allows the examination of molecules responsible for generating water flux. In particular, Na/K ATPase (NKA) has been implicated in directional Na+ transport and generation of water flow [13]. In kidney cells, NKA is polarized and accumulates in the basal-lateral surface. Blocking NKA by adding ouabain in the device's apical channel immediately decreased transepithelial flux and stall pressure (FIG. 3A-3C), whereas addition of Y-27367 which blocks ROCK kinase and myosin-II contractile activity, did not influence fluid flux significantly. Comparing IF images of cells in MFKP at ΔP=0 and ΔP=ΔP* (FIG. 3D-3M) showed similar F-actin distribution, but NKA showed reduced enrichment at the baso-lateral surface when ΔP=ΔP* (FIG. 3D-3O). In contrast, in MDCK II domes, NKA also showed a similar reduction in enrichment on the baso-lateral domain when the dome is stable (Extended Data FIG. 4F-4G). These results indicate that cells may actively sense the apical-basal pressure difference and modulate NKA localization.

Next, it was considered whether the device is useful for understanding fluidic pumping by primary human normal kidney and ADPKD cystic cells. AQP2, Na/K ATPase and Factin stains for wild type cortical cells (WTc), wild type medulla cells (WTm) and cystic cells (ADPKD) in MFKP showed the same distribution and morphology as those obtained from their corresponding immunohistochemistry images of kidney tissue sections (FIG. 13A-13D, 13F-13K), suggesting that the device is capable of capturing the general organization of these different types of epithelia. The barrier function of the epithelia was again assessed using dye permeation assay (FIG. 15A-15I).

Figures 4A, 4O:
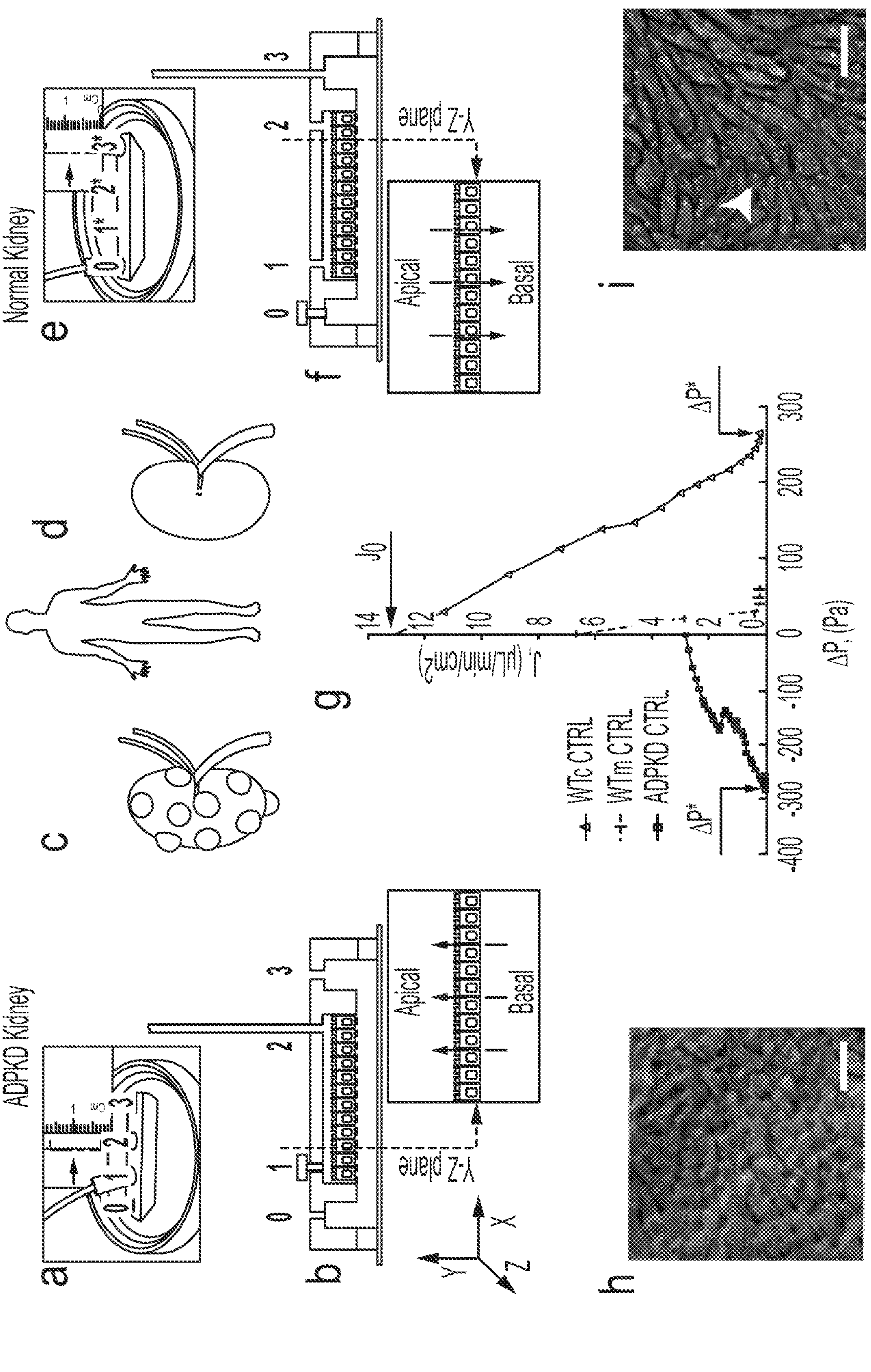
FIGS. 4A-4O are graphs and images showing fluid pumping performance of cells derived from Autosomal dominant polycystic kidney disease (ADPKD) patients as assayed in a microfluidic system according to an embodiment of the invention.
Figures 4A, 4O:
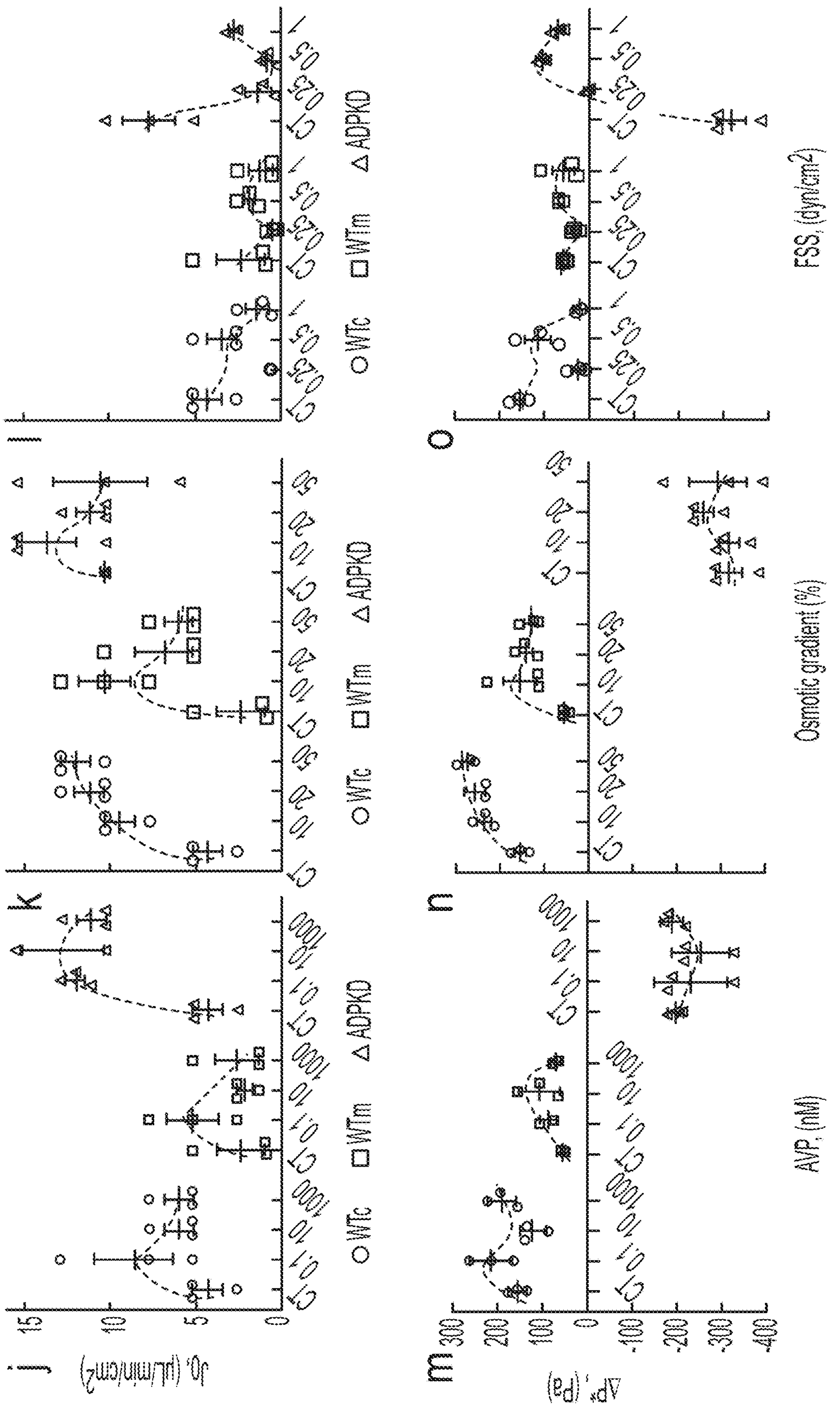

Once grown in the device, as with MDCK-II epithelium, apical to basal fluid flux was observed as a function of hydrostatic pressure gradient in WTc and WTm epithelium, resulting in a similar PPC (FIG. 4G). J0 and ΔP* was higher in case of WTc as compared to WTm (FIG. 4J-4O). Unlike absorptive function of normal kidney cells, ADPKD cystic cells had a secretory phenotype even though there is no dramatic difference in typical markers of apical-basal polarity [9,14]. The reversal of fluid flux in cystic cells remains unexplained and the underlying physical parameters of reversal have not been previously quantified. When the MC is connected to port 2 instead of port 3, fluid rises in the MC beyond the equilibrium height were observed, indicating basal-to-apical fluidic pumping. In both normal and ADPKD cells, the trans-epithelial fluid flux (J) and the PPCs are modulated by mechanical (FSS), chemical (AVP) and apical hypoosmotic (OSMO) perturbations. These changes were quantified by plotting J0 and ΔP* under different conditions (FIG. 4J-4O).

The device revealed that for WTc, WTm and ADPKD cells, J0 and ΔP* showed variable response to basolateral treatment of AVP (FIG. 4J, 4M). The observed massive surge in basal-to-apical fluid pumping in ADPKD epithelium matches studies in mouse models of ADPKD, indicating cysts grow bigger with AVP treatment [15]. ΔP* however remained constant at −300 Pa for ADPKD cells. Under apical hypo-osmotic treatment, proximal tubule cells (WTc) changed their pumping performance by increasing both J0 and ΔP*. WTm cells also increased J0 and ΔP* with apical hypo-osmotic shock (FIG. 4K, 4N). For ADPKD cells, while J0 increased with decreasing basal osmolarity, ΔP* didn't change and remained constant around-300 Pa (FIG. 4N). The converging nature of the PPC to a constant ΔP* for ADPKD epithelium (FIG. 15C) cannot be explained by the simple active flux model (FIG. 15F), suggesting differential mechanisms of regulation during fluidic pumping in wild type and ADPKD epithelium.

In both WTc and WTm cells, apical FSS for 5 hours did not change J0 or ΔP* significantly (FIG. 4L, 4O). At 1 dyn/cm2, both J0 and ΔP decreased for both WTc and WTm as compared to control cells. However, in case of ADPKD, even though increasing FSS resulted in a decrease in the average J0, the fluidic flux direction reversed under FSS (FIG. 4L) with ΔP* going from −300 Pa to 100 Pa (FIG. 4O).

Figures 5A, 5B, 5C, 5D, 5E, 5F, 5G, 5H, 5I, 5J, 5K, 5L:
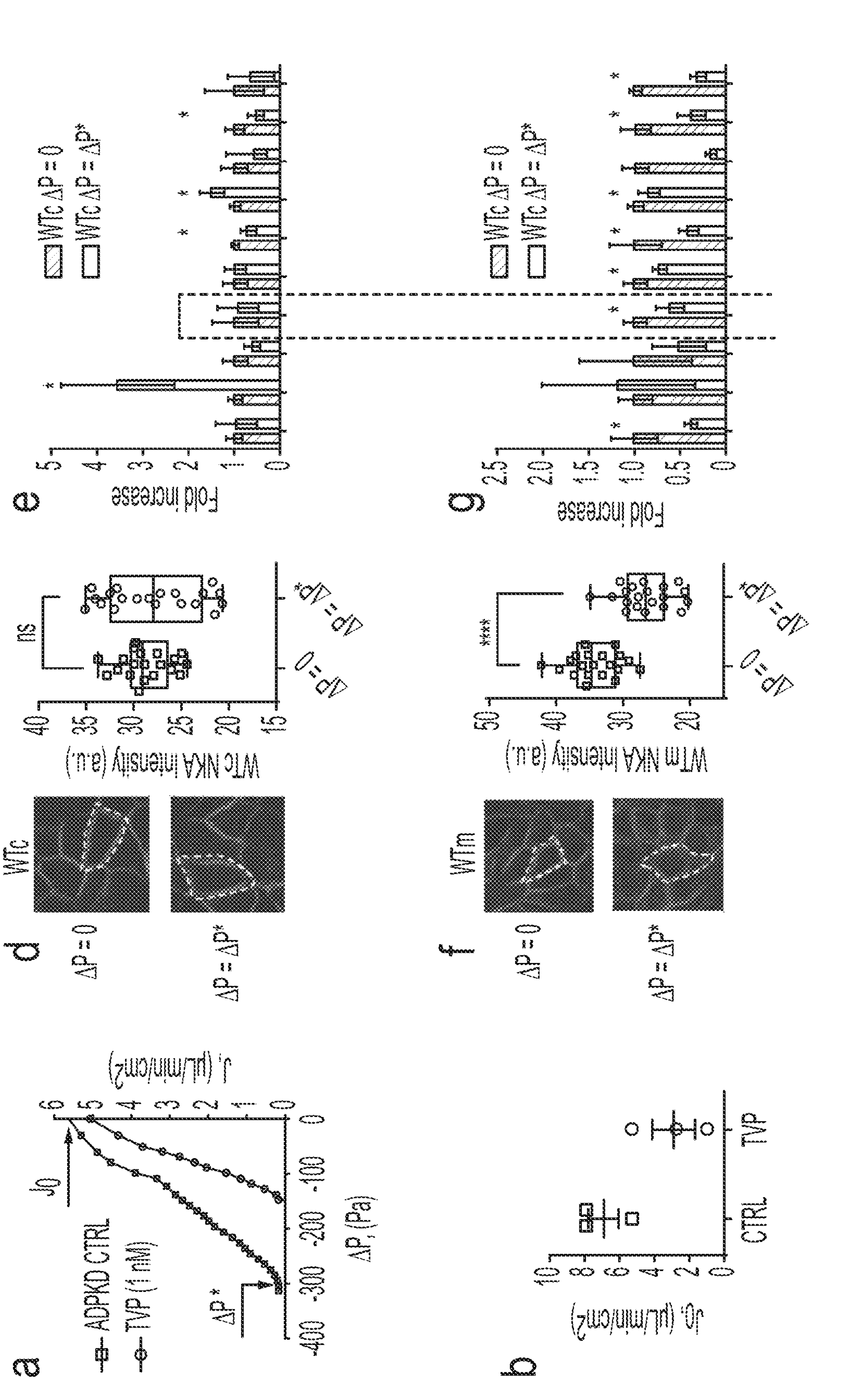
FIGS. 5A-5L are graphs and images showing that cystic cells have defects in sensing hydrostatic pressure as compared to normal cells.
Figures 5A, 5B, 5C, 5D, 5E, 5F, 5G, 5H, 5I, 5J, 5K, 5L:
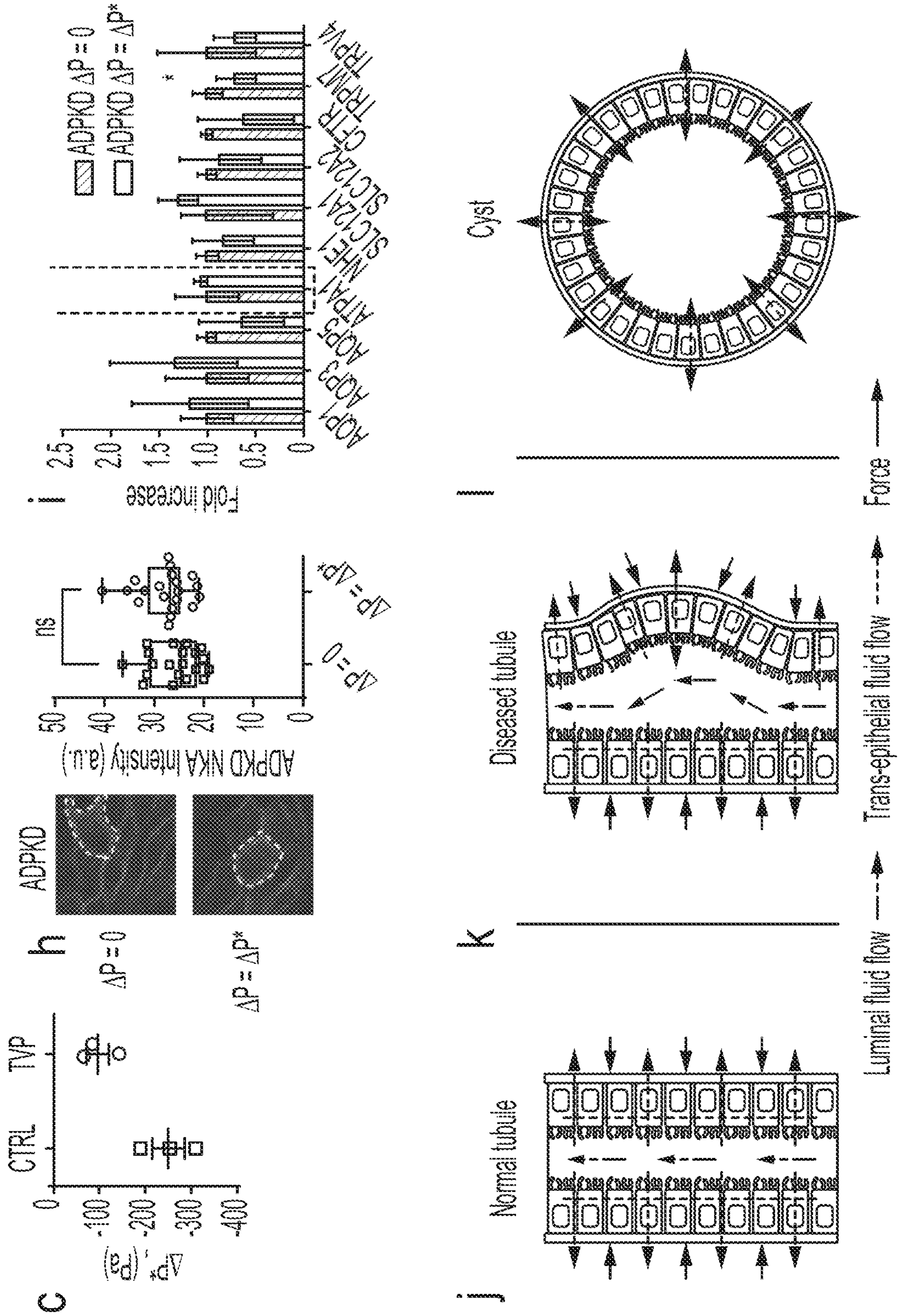
Figures 16A, 16B, 16C, 16D, 16E, 16F:
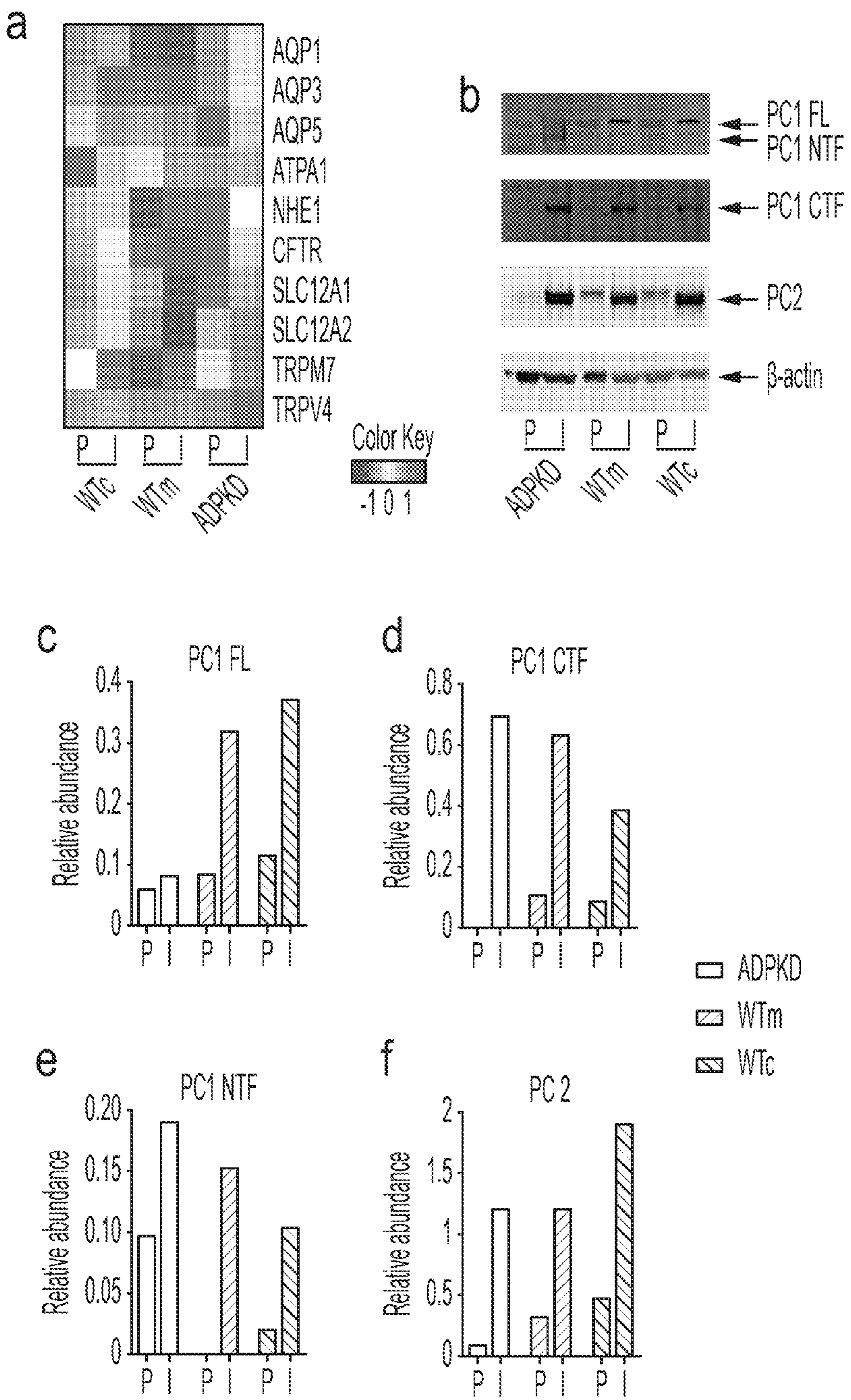
FIGS. 16A-16F are charts and graphs showing differential ion channel expression of normal and diseased cells grown in an MFKP as compared to impermeable substrates according to an embodiment of the invention

In ADPKD kidney, the progressive growth of fluid filled cysts leads to an increase in total kidney volume [16]. It has been shown that a hydrostatic pressure gradient (ΔP) is developed during fluid pumping, and the cyst wall must sustain a pressure of ~300 Pa. In the organ, this pressure points from the lumen towards the interstitium, and could drive cyst expansion. The regulation of ΔP* is important for understanding kidney morphogenesis. The Food and Drug Administration (FDA) approved Tolvaptan (TVP), which decreased the total kidney volume [16]. Tolvaptan is a V2R antagonist and has been shown to decrease CAMP levels [18]. Mature ADPKD epithelium in MFKP was treated with 1 nM TVP on the basolateral side for 1 hour and measured PPC. Interestingly, TVP decreased both J0 and ΔP* of the ADPKD epithelium as compared to the control (FIG. 5A-5C), confirming that the CAMP pathway can modulate fluid flux and ΔP*. To obtain a molecular profile of kidney cells during fluidic pumping, qPCR measurements for aquaporins (AQP1, AQP3 and AQP5), ion-pumps and exchangers (Na/K ATPase, NHE1, NKCC1, NKCC2, CFTR), and tension sensitive Ca2+ channels (TRPM7 and TRPV4) were taken, which are all potentially involved in regulating water and ion transport, and mechano-sensation. Heatmaps indicating the expression of mRNAs extracted from WTc, WTm and ADPKD cells grown on permeable substrate (MFKP) and on impermeable substrate (tissue culture treated polystyrene dishes) show substantial expression differences (FIG. 16A). Except for TRPM7 and TRPV4, expressions of all other genes were higher in cells grown in MFKP as compared to that on impermeable substrate. Moreover, using the device, changes in genes expression as a function of ΔP can be quantified. Cells from MFKP were collected under two conditions-AP=0 and ΔP=ΔP*. FIG. 5E, 5G, 5I) show that when exposed to stall pressure ΔP=ΔP*, WTm cells decreased the expressions of AQP1, AQP5, ATPA1, SLC12A1, SLC12A2, CFTR, TRPM7 and TRPV4.

ADPKD cells did not respond to ΔP*, where expressions of these genes either remained constant or increased slightly. IF images of F-actin and NKA in the MFKP device corroborates the qPCR results at ΔP=0 and ΔP=ΔP*. The total intensities of NKA in WTc, WTm and ADPKD epithelia under the two conditions were also consistent with the mRNA readings from qPCR (FIG. 5D, 5F, 5H). However, spatial arrangement of F-actin and NKA in WTc, WTm and ADPKD epithelia showed significant differences at ΔP=0 and ΔP=ΔP* (FIGS. 17A-17T, 18A-18T, and 19A-19T). For all the three human primary cell types, F-actin was generally the highest at the cell basal surface at ΔP=0, but the F-actin stress fiber density was significantly decreased at ΔP=ΔP* (FIG. 17A-17T, 18A-18T, and 19C, 19F, 190, 19Q). At ΔP* cells showed increase in F-actin intensity at the cell-cell junctions in WTc and ADPKD cells but not for WTm cells. Interestingly, ΔP* disrupted the apico-basal polarization of NKA in WTm cells (FIG. 18C-18F, 18P, 18R-18T). This depolarization effect was completely absent in WTc but was subtle in ADPKD cells exposed to ΔP*. This indicates that collecting duct cells (WTm population), may regulate trans-epithelial ion and fluid pumping by sensing hydrostatic pressure gradient.

The combined results offer insights into kidney fluidic pumping action and ADPKD cyst formation. FIG. 5J shows a section of a normal human kidney tubule. Arrows represent fluidic flux from the lumen into the interstitial space. Black arrows indicate the restoring force as a result of the fluidic pumping, arising from the apical-basal hydraulic pressure difference during pumping. Here the apical-basal pressure difference can prevent tubule expansion. During cyst initiation, due to altered morphology of the tubule, the local fluid shear stress can be lower, which leads to reversed direction of fluid pumping by ADPKD cells (FIG. 5K). This changes the direction of restoring force, which further destabilize the tubule. Together with aberrant pressure sensing response of ADPKD cells, act together to increase cyst outward pressure. These mechanical factors coupled with cell proliferation [19] can lead to gradual expansion of the cyst (FIG. 5L). The results demonstrate that secretory and absorptive functions of epithelia can generate significant mechanical forces, and maybe a general phenomenon in tubular morphogenesis in other contexts.

FIGS. 2A-2J: Fluid pumping performance of MDCK-II epithelium depends on mechanical, osmotic and chemical perturbation. (2A) A schematic representation of the Microfluidic Kidney Pump (MFKP). (2B) An image of the MFKP. Scale bar=1 cm. (2C) Longitudinal section of the device indicating four ports: 1 and 2 to access the apical channel and 0 and 3 to access the basal channel in the device. Black arrows indicate direction of fluid flux. Port 0 is closed except during seeding and cell culture. J1;2;3 are fluid fluxes and P1;2;3 are hydrostatic pressures at ports 1, 2 and 3, respectively. (2D) Dashed arrow shows a schematic of the cross-section of the device and a polarized epithelium. Papical and Pbasal indicates hydrostatic pressures in the apical and basal channels, and arrows indicate direction of trans-epithelial fluid flow. (2E) Dashed rectangle shows zoomed schematic of fluid flow in the microcapillary (MC) and a mm scale. The MC acts as a sensor to measure both J3 and P3. (2F) A snapshot of the MFKP setup inside an incubator for time-lapsed videography. The dashed line indicates MC, and 0, 1, 2 and 3 indicate ports in MFKP. Scale bar=1 cm. (2G) MDCK-II cells grown in MFKP generate a hydrostatic pressure gradient by pumping fluid from the apical to basal side. The height of fluid in the MC is plotted as function of time for MDCK-II epithelium in MFKP. Pumping actions of cells change under mechanical (FSS), chemical (AVP) and apical hypo-osmotic perturbations (OSMO). (2H) Pump performance curve (PPC) of MDCK-II epithelium showing trans-epithelial fluid flux (J) from apical to basal versus (ΔP=Pbasal−Papical) across the epithelium. J0 is the fluid flux at zero pressure gradient (ΔP=0) and ΔP* is the stall pressure when J=0. Both J0 and ΔP* change under FSS, AVP and OSMO perturbations. (i) J0 and ΔP* for MDCK-II epithelium under FSS, AVP and OSMO perturbations. (2J) Immunofluorescent (IF) images showing nucleus, F-actin, NKA and E-cadherin in MDCK-II epithelium grown in the MFKP. The dashed line (white) in the XZ panel indicate the porous membrane. The intensity projection for XZ images was recorded along the corresponding dashed lines in the XY images. Scale bar=25 um.

Figures 3A, 3O:
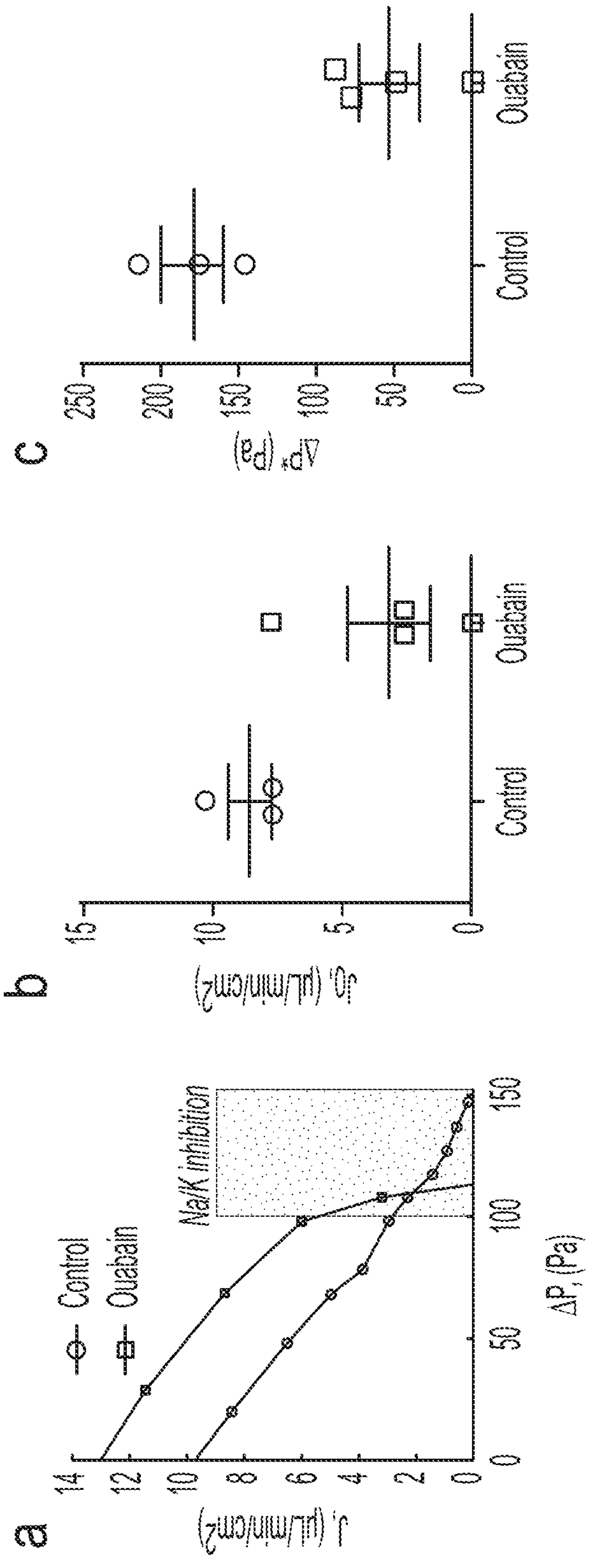
FIGS. 3A-3O are graphs and images showing fluid pumping performance of cells as assayed in a microfluidic system according to an embodiment of the invention.
Figures 3A, 3O:
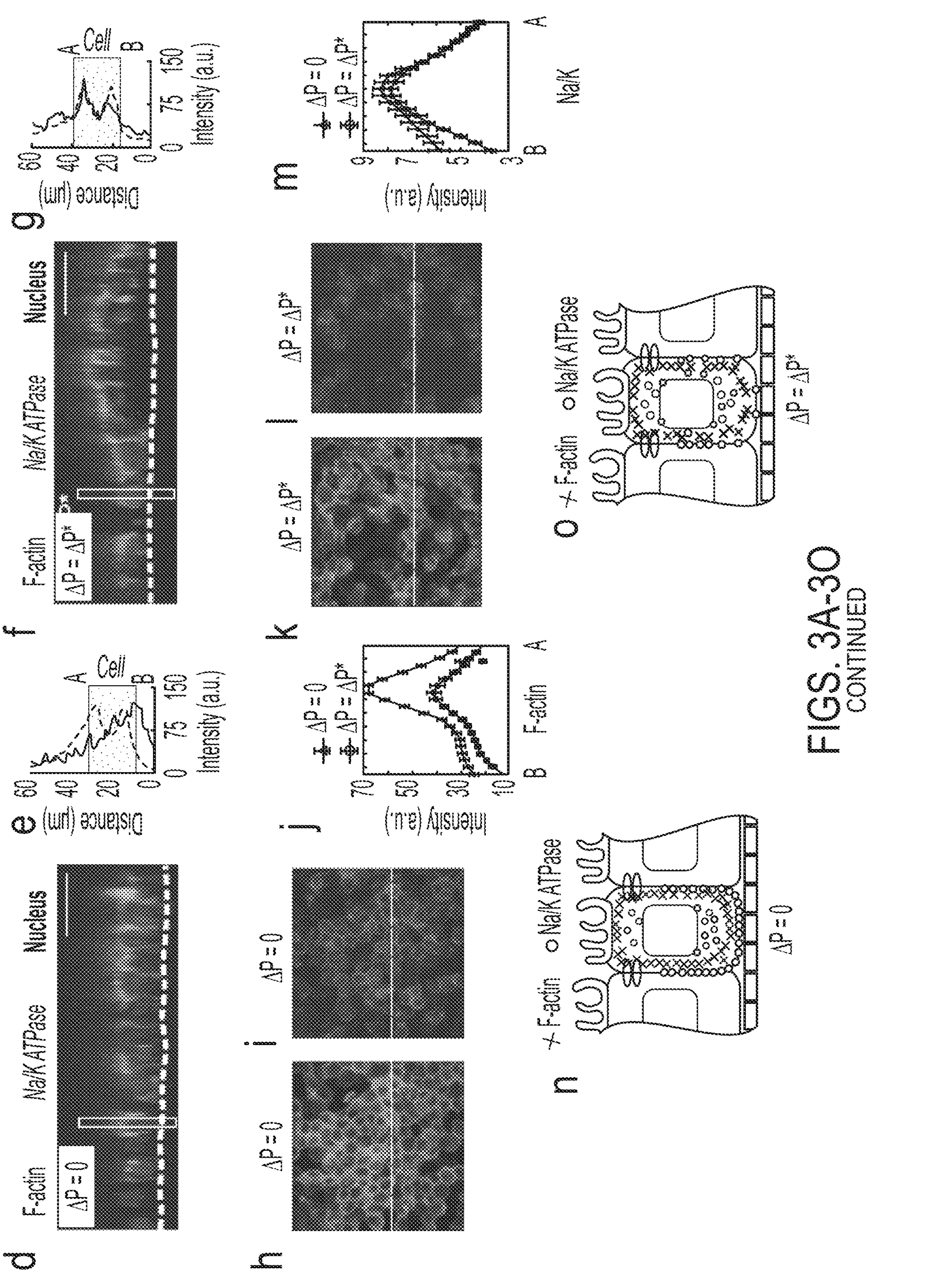

FIGS. 3A-3O: MDCK-II cells decrease the cortical expression of NKA at stall pressure (3A) Pump performance curves of MDCK-II cells with and without 0.2 μM of Ouabain. (3B-3C) Comparison of J0 and ΔP* for MDCK-II epithelium in control and 0.2 μM Ouabain treatment. (2D) XZ confocal section of MDCK-II epithelium in MFKP showing colocalization of F-actin, NKA at zero hydrostatic pressure gradient (or ΔP=0). The white dashed line represents the porous membrane. (3E) IF intensity profiles of F-actin and NKA along the band in d in arbitrary units (a.u.). The rectangle indicates location of cell, A and B indicate apical and basal surface of the cell under consideration. (3F) XZ confocal section of MDCK-II epithelium in MFKP showing colocalization of F-actin, NKA in the cells at stall pressure (or ΔP=ΔP*=200 Pa). The white dashed line represents the porous membrane. (3G) Intensity profiles of Factin and NKA along the band in 3F. (3H) Maximum intensity projected XY IF image of F-actin at ΔP=0. (3I) Maximum intensity projected XY IF image of NKA at ΔP=0. The dashed lines represent the line of the XZ projection in 3D. (3J) Comparison of the total intensity of F-actin in five cells chosen arbitrarily along the dashed line is plotted versus Z. B and A indicate the basal and apical surface of the cells. (3K) Maximum intensity projected XY IF image of F-actin at ΔP=ΔP*. (3L) Maximum intensity projected XY IF image of NKA at ΔP=ΔP*. The dashed lines represent the line of the XZ projection in 3F. (3M) Comparison of the total intensity of NKA in five cells chosen arbitrarily along the dashed line plotted versus Z. (3N) Schematic showing colocalization of F-actin and NKA in cells in MFKP at ΔP=0. (o) At ΔP=ΔP* there is a reduction in cortical NKA in the baso-lateral side.

FIGS. 4A-4O: Cystic cells derived from ADPKD patients pump fluid in the opposite direction as normal human kidney cells (4A) A snapshot of MFKP with MC connected to port 2. Port 1 is closed. (4B) Schematic of the setup, which allows measurement of trans-epithelial fluid flux from the basal to apical chamber. (4C) Schematic representation of a cystic kidney derived from ADPKD patients. (4D) Schematic representation of a kidney derived from normal human patients. (4E) The MC is connected to port 3 in the MFKP. Port 1 is closed. (4F) This setup enables measurement of trans-epithelial fluid flux from apical to basal chamber. (4G) Comparison of the pump performance curves of WTc, WTm and ADPKD epithelium grown in MFKP. The trans-epithelial fluid flux (J) decreases with increase in hydrostatic pressure gradient (ΔP) across the epithelium. J0 is the fluid flux at zero pressure gradient across the epithelium (ΔP=0) and ΔP* is the stall pressure when J=0. (4H) DIC image of ADPKD cells forming a mature epithelium on porous membrane in the device. Arrow indicates pores (1 μm) in the membrane. (4I) DIC image of WTc cells forming a mature epithelium on the porous membrane in the device. Comparison of J0 in WTc, WTm and ADPKD cells with varying AVP (j), hypo-osmotic gradient (4K) and fluid shear stress (4L). Comparison of ΔP* in WTc, WTm and ADPKD cells with varying AVP (4M), hypo-osmotic gradient (4N) and fluid shear stress (4O). For ADPKD cells, the fluid shear stress is applied on the basal side of the epithelium.

FIGS. 5A-5L: Cystic cells have defects in sensing hydrostatic pressure as compared to normal cells (5A) Comparison of fluid pumping performance of untreated (CTRL) ADPKD cells and ADPKD cells treated with 1 nM Tolvaptan (TVP) for 1 hour in the basolateral domain in MFKP. (5B) Comparison of J0 in CTRL and TVP. (5C) Comparison of stall pressure (ΔP*) for CTRL and TVP. Three biological repeats are performed for each condition. (5D) IF images of NKA in WTc cells at ΔP=0 and ΔP=ΔP* (~200 Pa). Plot showing total expression of NKA in WTc cells at ΔP=0 and ΔP=ΔP* (ns=not significant, p=0:74). Total intensity was plotted for cells picked randomly from the maximum intensity projected IF image (shown using dashed lines). (5E) qPCR comparison of relative expression changes of genes in WTm cells at ΔP=0 and ΔP=ΔP*. (f) IF images of NKA in WTm cells at ΔP=0 and ΔP=ΔP*. Plot showing total expression of NKA in WTm cells at ΔP=0 and ΔP=ΔP* (p<0: 0001). (5G) qPCR comparison of relative expression changes of genes in WTm cells at ΔP=0 and ΔP=ΔP*. (5H) IF images of NKA in ADPKD cells at ΔP=0 and ΔP=ΔP*. Plot showing total expression of NKA in ADPKD cells at $\Delta P=0$ and $\Delta P=\Delta P^*$ (ns, p=0.13) (5I) qPCR comparison of relative expression changes of gene in ADPKD cells at $\Delta P=0$ and $\Delta P=\Delta P^*$. (5J) A schematic representation of a tubular section in the nephron of a normal human kidney. The arrows indicate re-absorptive fluid flux from the lumen into the interstitial space. The arrowheads indicate the force due to generated pressure gradient from fluid pumping by cells. The tubular structure is stabilized by the pumping pressure difference due to apico-basal fluid flux (radially in). (5K) During cyst initiation, cell proliferation can alter the tubule geometry and the local fluid flow pattern, results in a lowered FSS. ADPKD cells may respond by reversing the fluidic pumping direction as shown in FIG. 3O, which also reverses the pressure gradient that further destabilizes the tubule. (5L) In mature cysts, fluid pumping elevates pressure in the cyst and aids in cyst expansion.

REFERENCES

1. Taal, M., Chertow, G., Marsden, P., Skorecki, K., Yu, A. & Brenner B. (2011). The Kidney, 9th Ed.
2. Weinstein, A. M. (2000). Sodium and chloride transport: proximal nephron. *The kidney. Physiology and pathophysiology.*
3. Grantham, J. J., Ye, M., Gattone, V. H., & Sullivan, L. P. (1995). In vitro fluid secretion by epithelium from polycystic kidneys. *The Journal of clinical investigation,* 95 (1), 195-202.
4. Burg, M. B., & Orloff, J. (1968). Control of fluid absorption in the renal proximal tubule. *The Journal of clinical investigation,* 47 (9), 2016-2024.
5. Dasgupta, S., Gupta, K., Zhang, Y., Viasnoff, V., & Prost, J. (2018). Physics of lumen growth. *Proceedings of the National Academy of Sciences,* 115 (21), E4751-E4757.
6. Heisenberg, C. P., & Bellaiche, Y. (2013). Forces in tissue morphogenesis and patterning. *Cell,* 153 (5), 948-962.
7. Miroshnikova, Y. A., Le, H. Q., Schneider, D., Thalheim, T., Rubsam, M., Bremicker, N., & Balland, M. (2018). Adhesion forces and cortical tension couple cell proliferation and differentiation to drive epidermal stratification. *Nature cell biology,* 20 (1), 69.
8. Torres, V. E., & Harris, P. C. (2006). Mechanisms of disease: autosomal dominant and recessive polycystic kidney diseases. *Nature Reviews Nephrology,* 2 (1), 40.
9. Lever, J. E. (1979). Inducers of mammalian cell differentiation stimulate dome formation in a differentiated kidney epithelial cell line (MDCK). *Proceedings of the National Academy of Sciences,* 76 (3), 1323-1327.
10. Latorre, E., Kale, S., Casares, L., Gomez-Gonzalez, M., Uroz, M., Valon, L., . . . & Ladoux, B. (2018). Active superelasticity in three-dimensional epithelia of controlled shape. *Nature,* 563 (7730), 203.
11. Stroka, K. M., Jiang, H., Chen, S. H., Tong, Z., Wirtz, D., Sun, S. X., & Konstantopoulos, K. (2014). Water permeation drives tumor cell migration in confined microenvironments. *Cell,* 157 (3), 611-623.
12. Li, Y., Mori, Y., & Sun, S. X. (2015). Flow-driven cell migration under external electric fields. *Physical review letters,* 115 (26), 268101.
13. Kennedy, B. G., & Lever, J. E. (1984). Regulation of Na+, K+-ATPase activity in MDCK kidney epithelial cell cultures: Role of growth state, cyclic AMP, and chemical inducers of dome formation and differentiation. *Journal of cellular physiology,* 121 (1), 51-63.
14. Wilson, P. D. (2004). Polycystic kidney disease. *New England Journal of Medicine,* 350 (2), 151-164.
15. Wang, X., Wu, Y., Ward, C. J., Harris, P. C., & Torres, V. E. (2008). Vasopressin directly regulates cyst growth in polycystic kidney disease. *Journal of the American Society of Nephrology,* 19 (1), 102-108.
16. Grantham, J. J., & Torres, V. E. (2016). The importance of total kidney volume in evaluating progression of polycystic kidney disease. *Nature Reviews Nephrology,* 12 (11), 667.
17. Torres, V. E., Chapman, A. B., Devuyst, O., Gansevoort, R. T., Grantham, J. J., Higashihara, E., & Czerwiec, F. S. (2012). Tolvaptan in patients with autosomal dominant polycystic kidney disease. *New England Journal of Medicine,* 367 (25), 2407-2418.
18. Gattone II, V. H., Wang, X., Harris, P. C., & Torres, V. E. (2003). Inhibition of renal cystic disease development and progression by a vasopressin V2 receptor antagonist. *Nature medicine,* 9 (10), 1323.
19. Gudipaty, S. A., Lindblom, J., Loftus, P. D., Redd, M. J., Edes, K., Davey, C. F., & Rosenblatt, J. (2017). Mechanical stretch triggers rapid epithelial cell division through Piezo1. *Nature,* 543 (7643), 118.

Example 3

Figure 6:
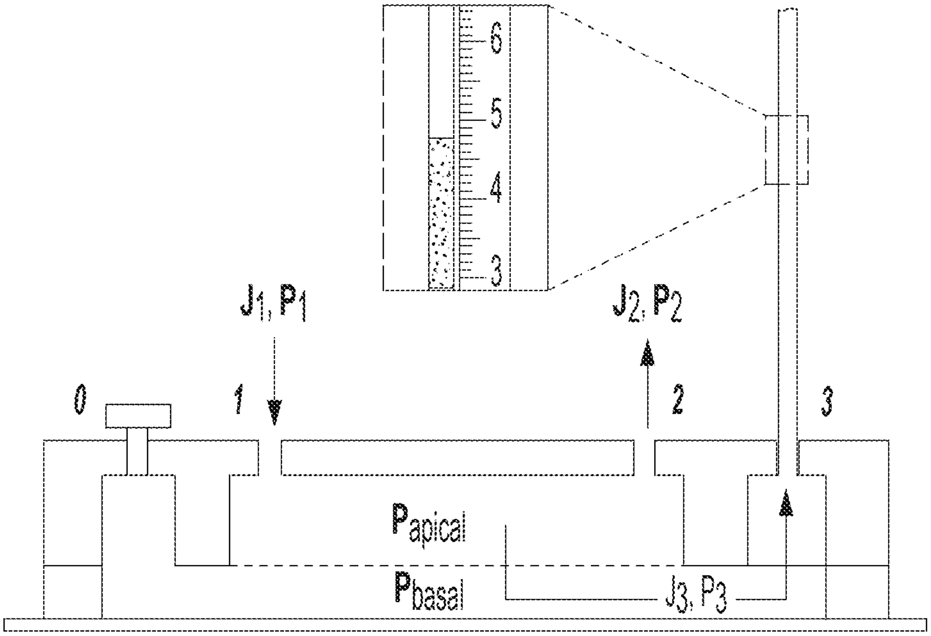
FIG. 6 is a schematic illustration of a microfluidic device for measuring a fluidic flux through a tissue layer according to an embodiment of the invention.

FIG. 6: Schematic of the longitudinal cross-section of MFKP without cells. Dashed box indicates a zoomed section of the fluid flow in the MC and a mm scale. J1 and P1 are the fluid flux and hydrostatic pressure at port 1, J2 and P2 are the fluid flux and hydrostatic pressure at port 2, J3 and P3 are the fluid flux and hydrostatic pressure at port 3.

The hydraulic pressure profile in the apical channel of MFKP was measured under different physiologically relevant fluid shear stress (FSS) and hydrostatic pressure gradients across the device. Fluid flow rate (Q) in the apical channel was changed using a syringe pump connected to port 1 and FSS was calculated using:

$$\tau = \frac{6\mu Q}{ab^2} \tag{1}$$

where t is the fluid shear stress, u is the fluid viscosity, Q is the flow rate, a is the width and b is the height of the channel. Fluid flow in the apical channel is due to the pressure gradient developed by the syringe pump between port 1 and 2 in order to maintain a constant flow rate (FIG. 6). Here, J1, J2 and J3 are the fluid fluxes through port 1, 2 and 3 and P1, P2 and P3 are hydrostatic pressures at port 1, 2 and 3 respectively. From mass balance, the fluid fluxes through the ports are linked according to Eq. 2:

$$J_1 = J_2 + J_3 \tag{2}$$

Figures 10A, 10B, 10C, 10D, 10E, 10F, 10G, 10H, 10I:
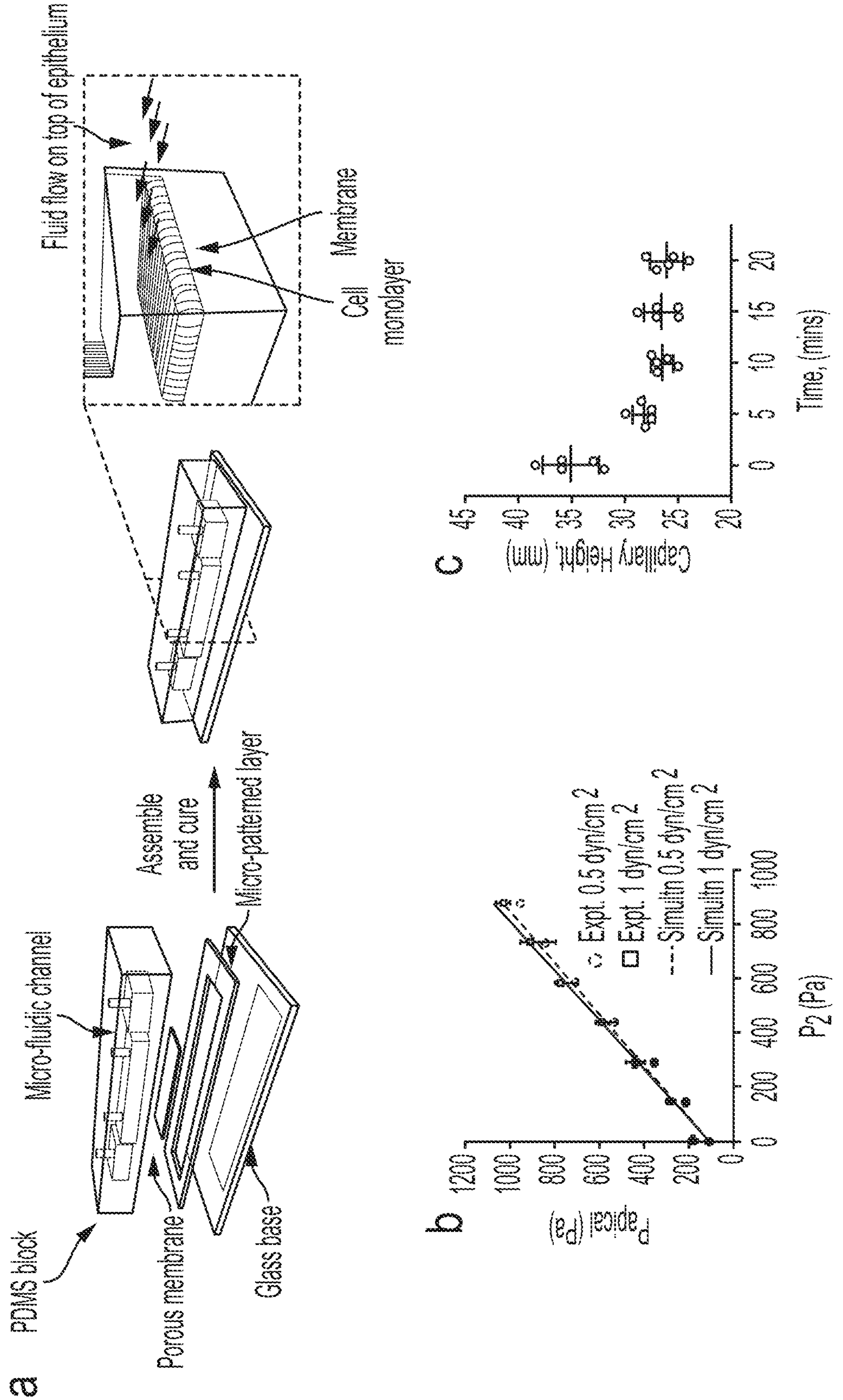
FIGS. 10A-10I are schematics showing fabrication and calibration of a Micro-fluidic Kidney Pump (MFKP) according to an embodiment of the invention.
Figures 10A, 10B, 10C, 10D, 10E, 10F, 10G, 10H, 10I:
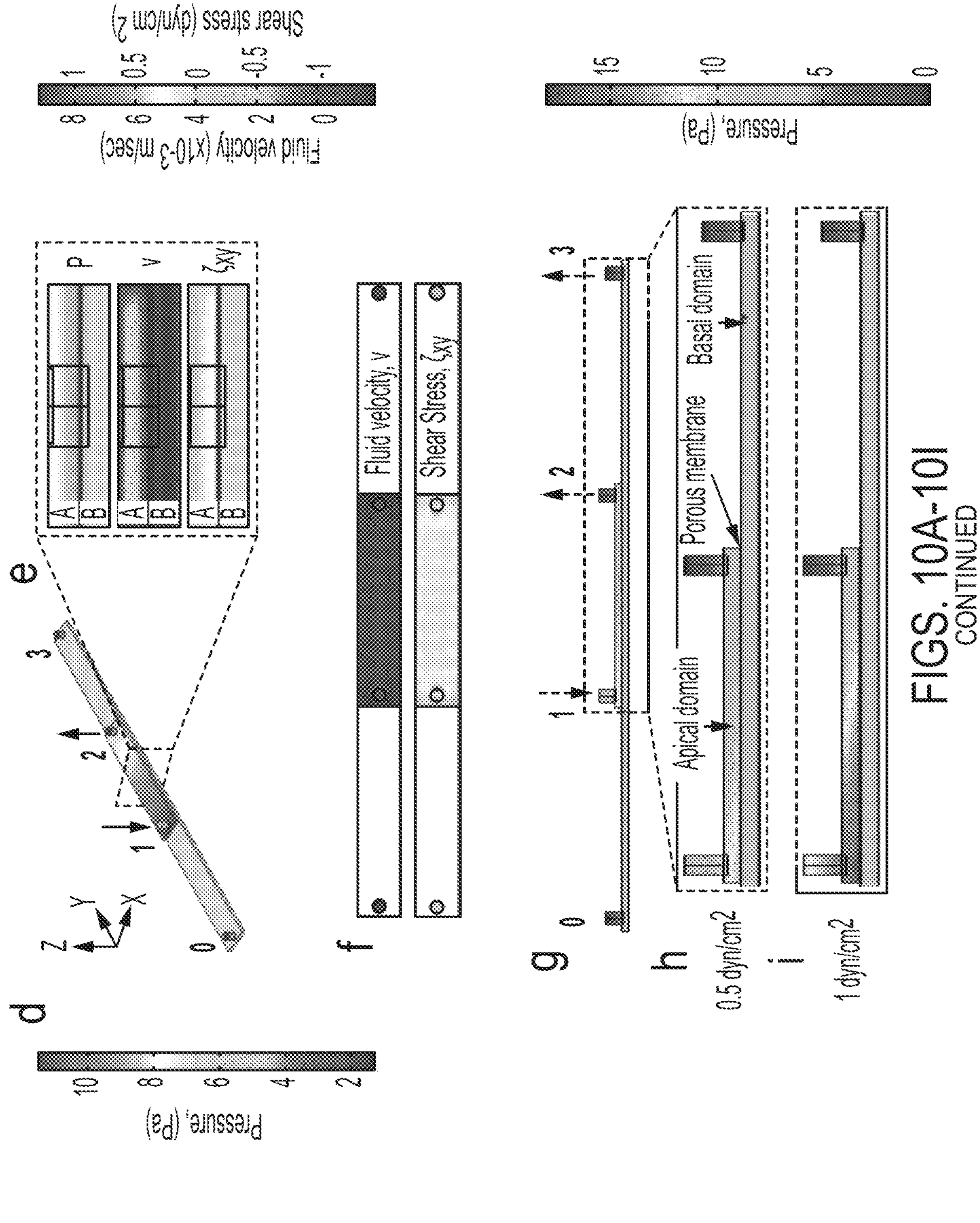

J1=Q is a known constant that is maintained by the syringe pump. P1, however is unknown. The average pressure in the apical channel (Papical) is greater than the basal channel ($P_{basal}$), which drives the apicalto-basal fluid flux, J3. When port 0 is closed, this fluid rises into the micro-capillary (MC) at port 3. Here MC acts as a sensor to measure both the fluid flux J3 and hydrostatic pressure P3 at port 3. At steady state, $P_{apical}$ is equal to $P_{basal}$ and J3=0. The height of fluid (h) in the MC at steady state was used to calculate the P3 using Eq. 3, which is also equivalent to the average basal hydrostatic pressure $P_{basal}$.

$$P_3 = \rho g h \quad (3)$$

while maintaining the same FSS, $P_{apical}$ can be changed by changing the exit pressure at port 2 (P2). P2 was varied by changing the height of the reservoir connected to port 2. By measuring the fluid height h in port 3 at J3=0, $P_{apical}$ was measured under two different FSS and multiple (P2) conditions (FIG. 10B). Horizontal error bars indicate same-device variation (mean±standard deviation, n=3) and vertical error bars indicate device-device variation (mean±standard deviation, n=5). MFKP can therefore be used to apply a variety of physiologically relevant FSS and hydrostatic pressure to an epithelium. Due to capillary action, fluid also rises in the MC without any excess pressure. Extra pressure can be adjusted for by measuring capillary height. The capillary height was measured for 5 different MCs with cell culture media. Error bars indicate standard deviation (n=5) (FIG. 10C).

Figure 7:
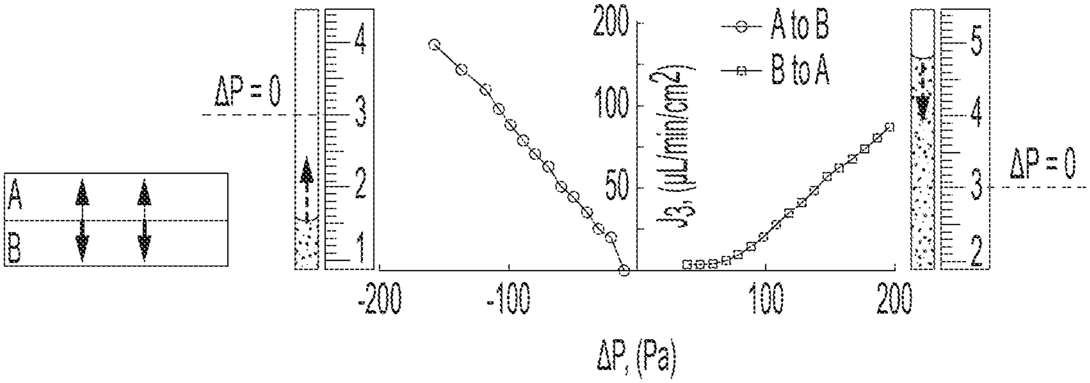
FIG. 7 is a plot showing apico-basal fluid flux J3 as a function of the trans-membrane hydrostatic pressure gradient ΔP without cells.

$P_{apical}$ was also measured under no FSS or P2 conditions using the same technique described in the previous section. Once $P_{apical}$ is known, the fluid flux J3 was plotted as a function of the pressure difference, $\Delta P = P_{basal} - P_{apical}$ in the absence of cells. When $P_{apical}$ is greater than $P_{basal}$, apical-to-basal (A to B) fluid flux decreases to zero as the system approached equilibrium i.e. ΔP=0, which is indicated with dashed a line in the MC schematic (left) (FIG. 7). When $P_{basal}$ is greater than $P_{apical}$, fluid flux in the MC reverses and Basal-to-apical (B to A) fluid flux also decreased to zero at ΔP=0 (FIG. 7). Slope of the J3-ΔP plot is related to the permeability of the porous membrane. The slope for the A-to-B is higher than that of B-to-A because, in case of A-to-B the fluid flow is due to both ΔP and capillary effect of the MC.

FIG. 7 is a plot showing apico-basal fluid flux J3 as a function of the trans-membrane hydrostatic pressure gradient ΔP without cells. The flux is in direction of the pressure gradient, and is zero when Pbasal=Papical.

To validate the experimental measurement of $P_{apical}$ in the device, the entire microfluidic device has been modeled using the COMSOL Multiphysics software. The system was divided into three domains; apical domain (A), porous membrane and basal domain (B) (FIG. 10D). Navier-Stokes equation (Eq. 4) was used to model the fluid domain in apical and basal channels and no slip boundary condition was enforced at the walls.

$$p(\vec{u}\cdot\nabla)\vec{u} = -\nabla p + \mu\nabla^2\vec{u} + \rho\vec{g}, \quad (4)$$

where ρ is density of the fluid, $\vec{\mu}$ is the velocity vector, p is the pressure, μ is the fluid viscosity and $\vec{g}$ is the acceleration due to gravity.

The following set of boundary conditions were used: Port 0: No Slip boundary condition as the port was blocked. Port 1: Flux boundary condition where flow velocity is prescribed. Two flow velocities were employed, namely, 0.0047 m/s and 0.0094 m/s corresponding to fluid shear stresses 0.5 and 1 dyn/$cm^2$.

Ports 2 and 3: The height of port 2 was varied in steps of 15 mm from an initial height of 10 mm. This was done to recapitulate the exact experimental condition wherein a reservoir was connected to port 2. During calibrations experiments, the exit pressure P2 was applied by changing the height of the reservoir.

Membrane-Channel interface: Velocity boundary conditions are used at the interface. For velocity parallel to the membrane surface, no slip zero velocity is imposed. For velocity perpendicular to the interface, a vertical velocity between 0-10 μm/s can be assigned. This models the fluid flow across the porous membrane. The computed pressure, velocity and shear stress profiles in the cross section of the device and on the surface of the porous membrane has been plotted using heat maps (FIG. 10D-10I). For both 0.5 and 1 dyn/cm2, the apical channel had a longitudinal pressure gradient (along the channel direction) of about 5 Pa. Moreover, flows across the membrane did not change the apical pressure significantly (~3 Pa). For simulations, $P_{apical}$ was calculated by taking average of the hydrostatic pressures in port 1 and 2 under all FSS and P2 conditions identical to the calibration experiment (FIG. 10B). Both experimental and simulation calibration data match closely at low P2. However, at large P2, the $P_{apical}$ shows a diverging trend with increase in FSS from 0.5 to 1 dyn/cm2. This is because increasing the exit pressure P2 causes an additional increase in the average pressure in the apical channel. Heatmaps show that the pressure (P), fluid velocity (v) and FSS (τ xy) are uniform along the XZ-crosssection (FIG. 10E). The hydrostatic pressure on the apical channel is higher than that of the basal channel. The fluid velocity is maximum at the center of the apical channel and both velocity and FSS are uniform along the width on top the porous membrane (FIG. 10F).

In order to validate whether P3 is equal to $P_{basal}$, pressure profile along the apical and basal channel in the YZ-axis was plotted. For both FSS 0.5 and 1 dyn/cm2, hydrostatic pressure below the membrane showed minimal spatial variation, and was similar to that of port 3 (FIG. 10G-10I), indicating that Eq. (3) is accurate for measuring P3. In summary, device has been calibrated experimentally and by using FEM model for hydraulic pressure profiles in both the apical and the basal channels. Once calibrated, the device accurately reports $P_{apical}$ and $P_{basal}$ within of ±10 Pa.

Barrier Strength of the Epithelium in MFKP

FIGS. 8A-8D are graphs showing variation of the trans-epithelial electrical resistance (TEER) with the number of days post confluence for (a) MDCK II cells, (b) WTc cells, (c) WTm and (d) ADPKD cells.

Figures 11A, 11B, 11C, 11D, 11E, 11F:
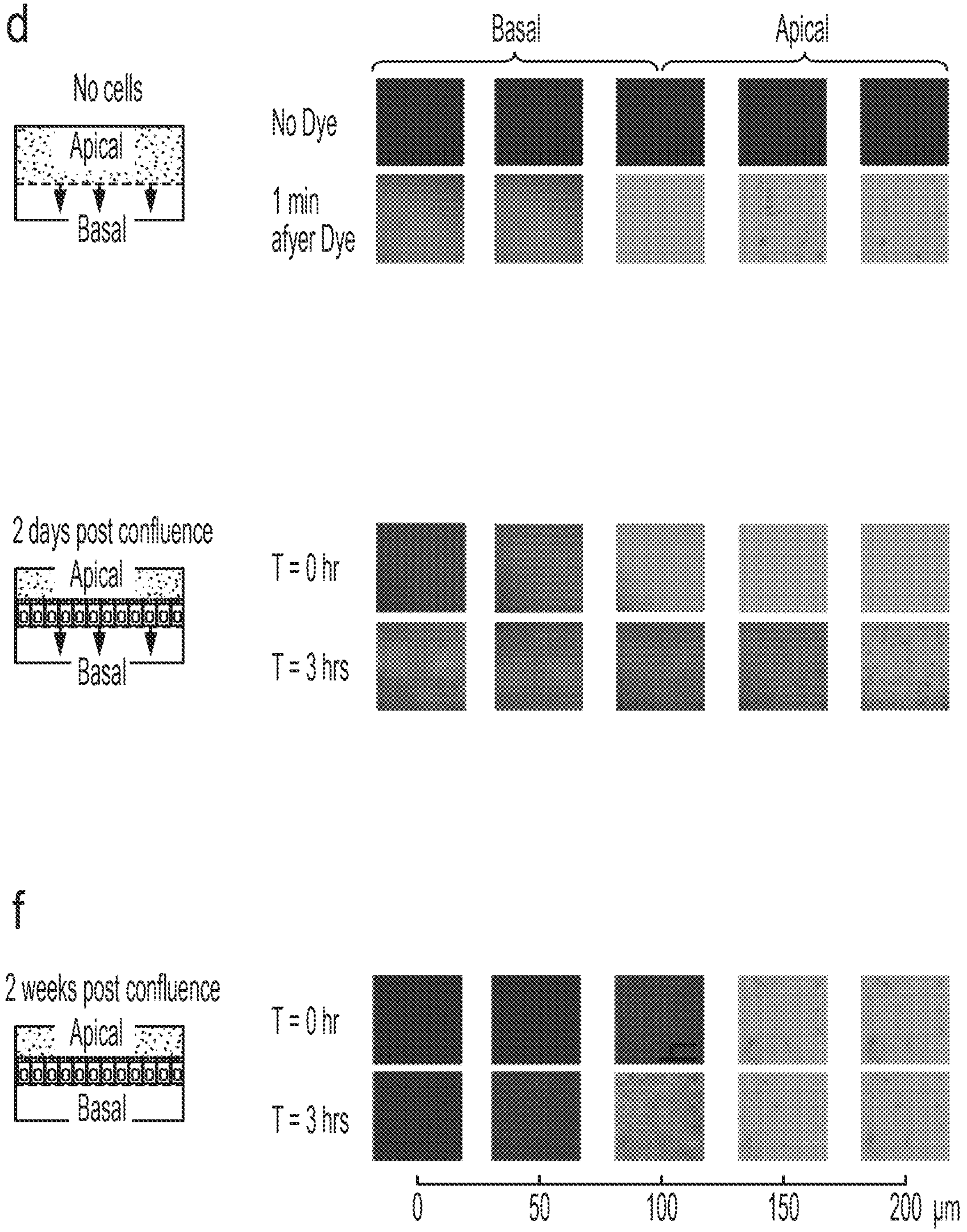
FIGS. 11A-11F are images and graphs showing that MDCK-II cells polarize to form strong apical-basal barrier in a MFKP according to an embodiment of the invention.

Trans-epithelial electrical resistance (TEER) is considered as the gold standard for estimating epithelial barrier strength [3]. However, in case of MFKP, off-the-shelf electrodes do not fit in the apical and basal channel in the device. Therefore, TEER values were recorded using standard Ag/AgCl electrodes by seeding cells on membrane filters pre-treated with fibronectin. MDCK-II cells showed a sharp rise in normalized TEER value of 220/cm2 in 3-4 days post confluence. This value then plateaued to 180/cm2 with time (FIG. 8A-8Da). This indicates that MDCK-II cells form a strong barrier post confluence. In the MFKP the barrier strength was quantified by using a FITC-conjugated dextran dye of MW 2000 kDa. The dye was dissolved in cell culture media at 5% v/v ratio and added to the apical channel through port 1 and 2 in the device and allowed to diffuse into the basal channel. Stacks of confocal fluorescence images, 20 μm apart, were taken spanning the basal and apical channels. The diffusion of the dye across the epithelium to the basal channel was measured by quantifying the temporal variation of the average relative intensity of the images. Upon addition of the dye into the device without cells, the intensity quickly increased within a minute of adding the dye to the apical channel, keeping the basal channel closed. Within 5 minutes the dye diffused completely into the basal channel. The dashed line was used to indicate the position of the porous membrane that separates the basal and apical side (FIG. 11A). This indicates that dye diffusion across the porous membrane is relatively quick (<10 min). For MDCK-II epithelium 2 days post confluence, it took about 3 hours for the dye to diffuse into the basal side from the apical side, indicating relatively poor barrier strength (FIG. 11B). In this case, comparison of the images of the basal and apical channel in the MFKP at T=0 hr and at T=3 hr indicated slow diffusion of the dye across the epithelium. However, For MDCK-II epithelium that is 2 weeks post confluence, the dye did not diffuse from the apical to basal channel at all. The average intensity of the images in the basal side remained the same after 3 hours post injection of dye into the apical channel (FIG. 11C). In this case, comparison of the fluorescence images of the basal and apical channel in MFKP at T=0 hour and at T=3 hours indicated no diffusion of dye across the epithelium.

Figures 8A, 8B, 8C, 8D:
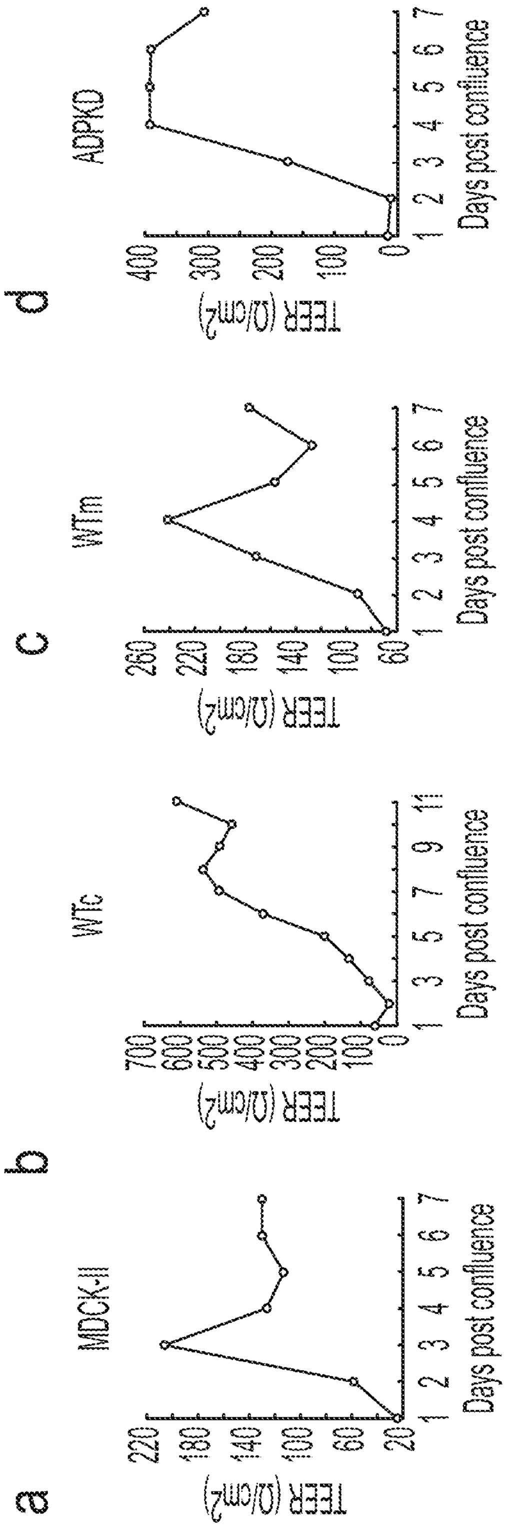
FIGS. 8A-8D are graphs showing variation of the trans-epithelial electrical resistance of the cells under consideration.
Figures 9A, 9B, 9C, 9D, 9E, 9F:
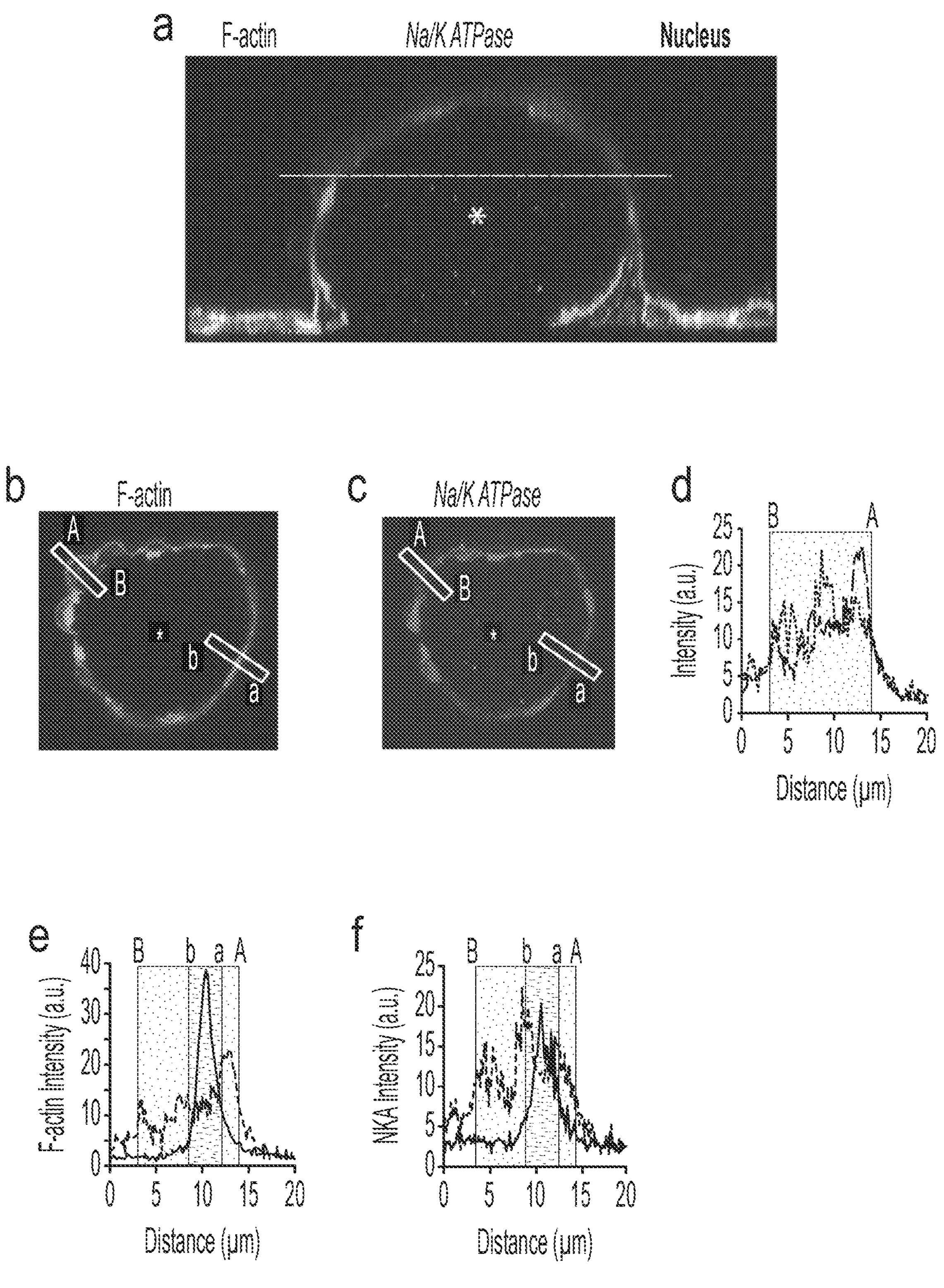
FIGS. 9A-9F are confocal images of epithelial domes on 2D impermeable substrate and graphs demonstrating polarization of proteins under consideration.

For human primary cells from both non-cystic and cystic kidneys, tissue samples were dissected from the cortex, medulla, or cortical cyst wall (see methods). The cells were labelled as wild type cortex (WTc), wild type medulla (WTm) and cystic (ADPKD) for all experiments. The cells were not passaged thereafter to avoid fibroblast overgrowth. The TEER values for WTc cells seeded on membrane filters reached a peak of 539 Ω/cm2 after 8 days post confluence and then plateaued (FIG. 8B). However, for both WTm and ADPKD cells the TEER values increased rapidly post confluence and plateaued at 180 and 350 Ω/cm2 (FIG. 8C, 8D). This indicates that both normal human kidney and PKD cystic cells exhibit strong barrier function on porous substrates. The steady state TEER value for some batch of cells reached as high as 854.22 Ω/cm2 for WTc cells (plot not shown) and 526.5 Ω/cm2 for WTm cells (two biological repeats for both WTc and WTm cells). However, sample-to-sample variability was higher for WTm cells. To measure the barrier strength of primary cells in MFKP, cells were seeded at high density by thawing directly from frozen vials. Cells grew to confluence in 2-3 days and then MFKPs were perfused with media every day for the next 2 weeks to form a strong barrier between the apical and basal channel. In all three cell types, the FITC dye did not diffuse from the apical to basal channel. The average fluorescence intensity of the basal channel remains the same as without dye after 3 hours post injection in the apical channel (FIG. 14A-14C). The dashed white line is used to indicate the position of the porous membrane that separates the basal and apical channel. The variability of fluorescence intensity in the same device and from device to device was low (FIG. 14G-141). Horizontal error bars indicate same-device variability and vertical error bars indicate device-to-device variability (mean±standard deviation, n=3). In all three types of epithelia, fluorescence images of the basal and apical channels in MFKP at T=0 and at T=4 hr indicated no diffusion of the dye through these epithelia as shown in representative images (FIG. 14D-14F).

Figures 15A, 15B, 15C, 15D, 15E, 15F, 15G, 15H, 15I:
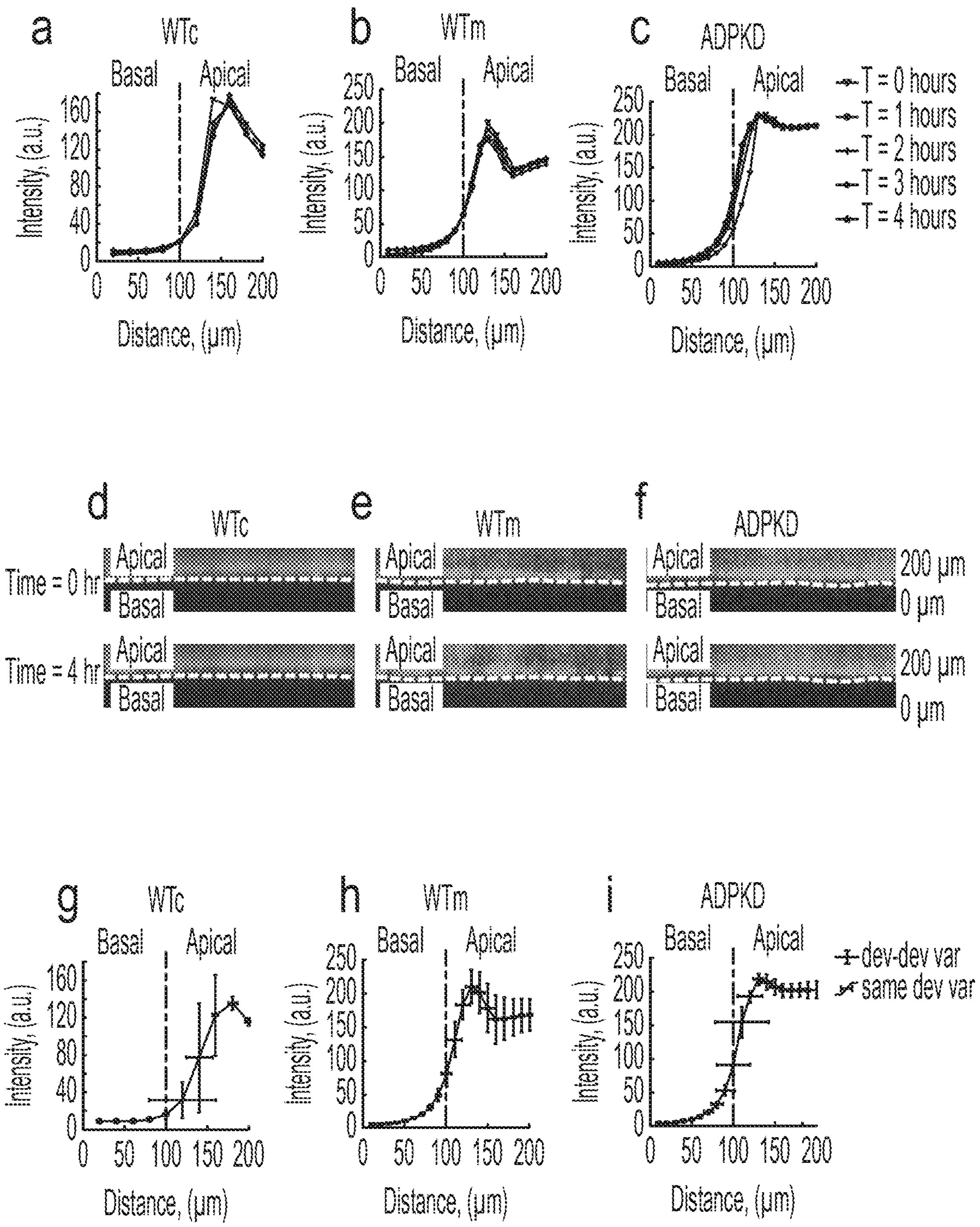
FIGS. 15A-15I are graphs showing that normal human kidney tubular epithelial and ADPKD cystic cells polarize to form strong apico-basal barrier in an MFKP according to an embodiment of the invention.

Simple Theoretical Model can Explain Increase in J0 and ΔP* with Apical Hypo-Osmolarity The experiments showed that the epithelial layer can actively pump fluid across the epithelium from the apical to basal sides. To mathematically describe this fluid pumping, a steady-state description and model the flow of water across the epithelium, driven by the passage of an idealized charge-neutral solute is considered. It is assumed that cells are stationary without translation or deformation. Each cell in the monolayer can be approximated as a cylinder with radius R0 and height L (FIG. 15D). The cell has an apical end (a) and a basal end (b). The direction points from the basal end to the apical end of a cell is defined as the x-direction. x=0 is the basal position while x=L is the apical position. It is assumed that the fluid flow and solute diffusion and convection only happens in the x-direction within each cell. Those happen through gap junctions are neglected.

In cylindrical coordinates, the Stokes' equation for cytoplasmic water flow in the cell is $$0 = -\frac{dp}{dx} + \mu\frac{1}{r}\frac{d}{dr}\left(r\frac{dv}{dr}\right), \tag{5}$$

where p is the intracellular hydrostatic pressure, μ is the dynamic viscosity of the fluid, and v is the velocity of the flow in the positive x direction. The spatial profile of v is $$v(x, r) = 2\overline{v}(x)\left[1 - \left(\frac{t}{R_0}\right)^2\right], \text{ where} \tag{6}$$

$$\overline{v}(x) = \frac{1}{\pi R_0^2}\int_0^{R_0} v(r, x)2\pi r dr \tag{7}$$

is the averaged velocity in each cross section.

Eq. 6 results from the non-slip boundary condition at the cell cortex. Substituting Eq. 6 into Eq. 5 gives $$0 = -\frac{dp}{dx} - \frac{8\mu}{R_0^2}\overline{v}. \tag{8}$$

The conservation of mass requires $$\frac{dv}{dx} = 0, \tag{9}$$

which suggests that $\vec{v}$ must be a constant in x. In this case, p must be linear in x as seen from Eq. 8. Only the pressure at the apical end is needed, $p^a = p|x=L$, and the pressure at the basal end, $p^b = p|x=0$, to know the profile of the intracellular pressure p. The average velocity of the intracellular flow can also be solved from $p^a$ and $p^b$ by using Eq. 8, i.e., $$\overline{v} = -\frac{R_0^2}{8\mu L}(p^a - p^b), \tag{10}$$

so that $\vec{v}$ is not an unknown from modeling point of view.

Cross-membrane water fluxes occur at the apical and the basal surfaces due to an osmotic gradient of the idealized solute (mainly Na+). The convention is that water fluxes are positive from outside to inside the cell. The continuity relation requires $$\overline{v} = -J^a_{water} = J^b_{water}, \tag{11}$$

which gives two equations to solve for $p^a$ and $p^b$.

To find the water flux, a model for the solute concentration, c, is needed. The steady-state equation for solute diffusion is $$\frac{d}{dx}\left(-D\frac{dc}{dx}+\overline{v}c\right)=0. \tag{12}$$

So that the intracellular solute flux $$J_c=-D\frac{dc}{dx}+\overline{v}c \tag{13}$$

must be a constant throughout the cell. This constant is determined by solute boundary fluxes at the apical and basal surface. It is also assumed that solute fluxes are positive inwards.

At the cell apical and basal boundary, the solute flux is composed of a passive part, $J_{c;passive}$, and an active part, $J_{c;active}$ [5], $$J_c|_{x=L}=-J_c^a=-\left(J_{c,passive}^a+J_{c,active}^b\right), \tag{14}$$

$$J_c|_{x=0}=J_c^b=J_{c,passive}^a+J_{c,active}^b, \tag{15}$$

where the passive flux follows the gradient of solute concentration across the cell membrane, i.e., $$J_{c,passive}^i=-g^i\left(c^i-c_0^i\right),\ i=\{a,b\}, \tag{16}$$

where g is the coefficient of passive ion flux, $c^a=c|_{x=L}$, $c^b=c|_{x=0}$, and $c_0$ is the solute concentration outside of the cell. The expression for the active solute fluxes vary depending the types of solute, the cell type and potential active regulation by the cell, and is discussed below. Equations 14 and 15 serve as two boundary conditions for Eq. 12.

The water flux across the cell surface is determined by both the hydrostatic pressure gradient and solute osmotic gradient:

$$J_{water}^i=-\alpha^i\left(\Delta p^i-RT\Delta c^i\right),\ i=\{a,b\}, \tag{17}$$

where α is the coefficient of water permeation, which can be different at the apical and the basal ends of the cell, R is the ideal gas constant, T is the absolute temperature, and $$\Delta p^i=p^i-p_0^i,\ \Delta c^i=c^i-c_0^i,\ i=\{a,b\}, \tag{18}$$

a PPC as shown in FIG. 14E is acquired. (parallel lines). This models a simple solute pump where the flux is linearly proportional to the concentrate difference with a stall solute flux determined by $$\Delta\mu_c^{a,b}[6].$$

This model gives an increasing fluidic pumping stall pressure as a function of decreasing osmolarity of the apical fluid, as seen for WTc epithelium in FIG. 3N.

Alternatively, if the solute pumping flux has a pressure dependence, e.g., $$J_{c,active}^a=\gamma_c^aRT\left(c_{in}^a-c_0^a-\Delta\mu_c^a\right), \tag{19}$$
$$J_{c,active}^b=\gamma_c^bRT\left(c_{in}^b-c_0^b-\Delta\mu_c^b\right),$$

a PPC as shown in FIG. 14E is acquired. (parallel lines). This models a simple solute pump where the flux is linearly proportional to the concentrate difference with a stall solute flux determined by $$\Delta\mu_c^{a,b}[6].$$

This model gives an increasing fluidic pumping stall pressure as a function of decreasing osmolarity of the apical fluid, as seen for WTc epithelium in FIG. 3N.

Alternatively, if the solute pumping flux has a pressure dependence, e.g., $$J_{active}^a=\gamma^a\frac{c^b-c^a}{c_{0,r}}k_p\left(p_0^b-p_{0,r}\right), \tag{20}$$
$$J_{active}^b=\gamma^b\frac{c^b-c^a}{c_{0,r}}k_p\left(p_0^b-p_{0,r}\right),$$

a PPC as shown in FIG. 14F is observed. (converging lines). In this case, the stall pressure, ΔP* of the epithelium is insensitive to osmolarity of the apical fluid, as seen for ADPKD epithelium in FIG. 3N.

The model described here is phenomenological in nature, and does not include electrical charges of different species of ions. There is likely a strong coupling between different types of solutes, and a full molecular model is considerably more complex. Nevertheless, the model demonstrates that the basic physics of fluid flow across the epithelium coupled with active solute flow should produce active pumping behavior, as seen in experiments. Moreover, the observed stall pressure is probably due to a combination of active-flux dependence on osmolarity and pressure regulation of active flux. This is supported by observed changes in the localization of NaK ATPase (NKA) as a function of pressure. Therefore, a full molecular model will require understanding of how hydraulic pressure regulates active solute flux.

MDCK-II Domes as Three Dimensional Epithelial Pressure Vessels

Validation of ΔP Measured in MFKP Using MDCK-II Domes

To validate the apical-basal pressure difference measured for MDCK-II epithelium in MFKP, fluid-filled domes seen in mature polarized MDCK-II monolayer on 2D impermeable substrates (glass) were assayed. Domes (or blisters) are likely developed due to trans-epithelial pumping of ions and water following a similar mechanism. The three dimensional hemi-spherical shape is sustained by the hydrostatic pressure gradient developed (ΔPdome) [1]. The ΔPdome was measured by inserting a glass micro-needle-based pressure sensor into MDCK-II domes (FIG. 12A, 12B). The micro-needle has an oil-water interface with a known surface tension and the other end of which is connected to a pressure sensor (FIG. 12C). By measuring the interfacial curvature, the hydrostatic pressure in the dome can be calculated using Young-Laplace equation (Eq. 21). Further details of the exact working principle of this device is described elsewhere [2]

$$P_1 - P_2 = \frac{2\gamma}{R}, \tag{21}$$

where P1-P2 is the pressure difference across the oil-media interface, is the oil-media surface tension for the interface, and R is the mean radius of curvature of the oil-media interface (FIG. 12C). Since P1 is the pressure inside the dome, knowing the hydrostatic pressure in the media then gives $\Delta P_{dome}$. $\Delta P_{dome}$ in MDCK-II domes of varying size was determined to be in similar range as that measured in case of the MFKP (FIG. 12D, 12E). Note this method does not simultaneously measure fluid flux across the epithelium, therefore it is not known which part of the PPC curve the measurement is probing. However, the method provides estimates on upper bounds in dome pressure. These results, together with traction force measurements of pressure inside the same type of domes [4], show that MDCK-II epithelium can develop hydrostatic pressure of the order of 200 Pa.

Role of Hydrostatic Pressure Gradient on the Baso-Lateral Localization of NKA

Mature MDCK-II domes in epithelia on 2D impermeable substrates (glass) were also used to investigate the effect of hydrostatic pressure gradient on the localization of F-actin and NKA in the cells forming domes. Cells that have just formed a lumen, referred to here as a pre-dome or unstable ($\Delta P_{dome} \approx 0$), with the cells experiencing high pressure (near stall pressure) in mature domes ($\Delta P_{dome} \approx \Delta P^*$) (FIG. 12F, 12G) were compared. Time lapse videos show that MDCK-II domes were unstable when the monolayer was immature, and were prone to collapse, likely due excessive fluid leakage. However, as the monolayer matures, the domes became stable and eventually reaching a steady size due to a stall pressure. It was hypothesized that hydrostatic pressure gradient can change the baso-lateral polarization of NKA, which then leads to the decrease in trans-epithelial fluid flux. In both cases the epithelium was a free-standing monolayer, hence the influence of substrate focal adhesions on the localization of NKA can be ignored. Confocal reconstruction of MDCK-II pre-dome showed enrichment of F-actin in the cortex and NKA primarily on the baso-lateral domain (FIG. 12H-12K). However, in case of cells in mature domes experiencing high pressure near stall, NKA expression was depleted in the basal domain (FIG. 12L-120). F-actin was still cortical in nature. By plotting the fluorescence intensity of each slice in the confocal stack versus the distance, it was determined that the overall intensity of both F-actin and NKA in the cells also decreased when the cells are experiencing near stall pressure (FIG. 12P, 12Q). Lattore et al. previously reported mechanical strain heterogeneity in MDCK cells forming domes of controlled sizes and cortical dilution of F-actin in super-stretched cells [4]. Therefore, to decouple the role of stretch from hydrostatic pressure, it was chosen to investigate relatively less stretched cells only. It was determined that both stretched and unstretched cells in mature domes exhibit depolarization of NKA (FIG. 9A-9F). Therefore these results are further evidence that the hydrostatic pressure gradient plays an important role in NKA polarization in MDCK-II cells.

FIGS. 9A-9F are confocal images and graphs. (9A) 3D confocal reconstruction of a mature MDCK-II dome stained for F-actin, NKA (α-sub-unit) and DNA. The asterisk indicates lumen in the dome. (9B) Cross-sectional IF image of F-actin along the dashed line in 9A. (9C) Cross-sectional IF image of NKA along the dashed line in 9A. (9D) Comparison of intensity profiles of F-actin and NKA from basal to apical side of a cell in 9B and 9C. The apical and basal domains of the cell are indicated by A and B. One line indicates F-actin intensity along the band in 9B and a second line indicates NKA intensity along the band in 9C. (9E) comparison of basal to apical intensity of F-actin in a stretched and unstretched cell in the dome in 9B. One line indicates the F-actin intensity along the ba band in 9B. The second line indicates the F-actin intensity along the AB band in 9B. (9F) Comparison of basal to apical intensity of NKA in a stretched and unstretched cell in the dome in 9B. One line indicates the NKA intensity along the ba band in 9B. The second line indicates the NKA intensity along the AB band in 9B. The apical and basal domains of the unstretched cell are indicated by A and B. The apical and basal domains of the stretched cell are indicated by a and b.

Figures 13A, 13B, 13C, 13D, 13E, 13F, 13G, 13H, 13I, 13J, 13K:
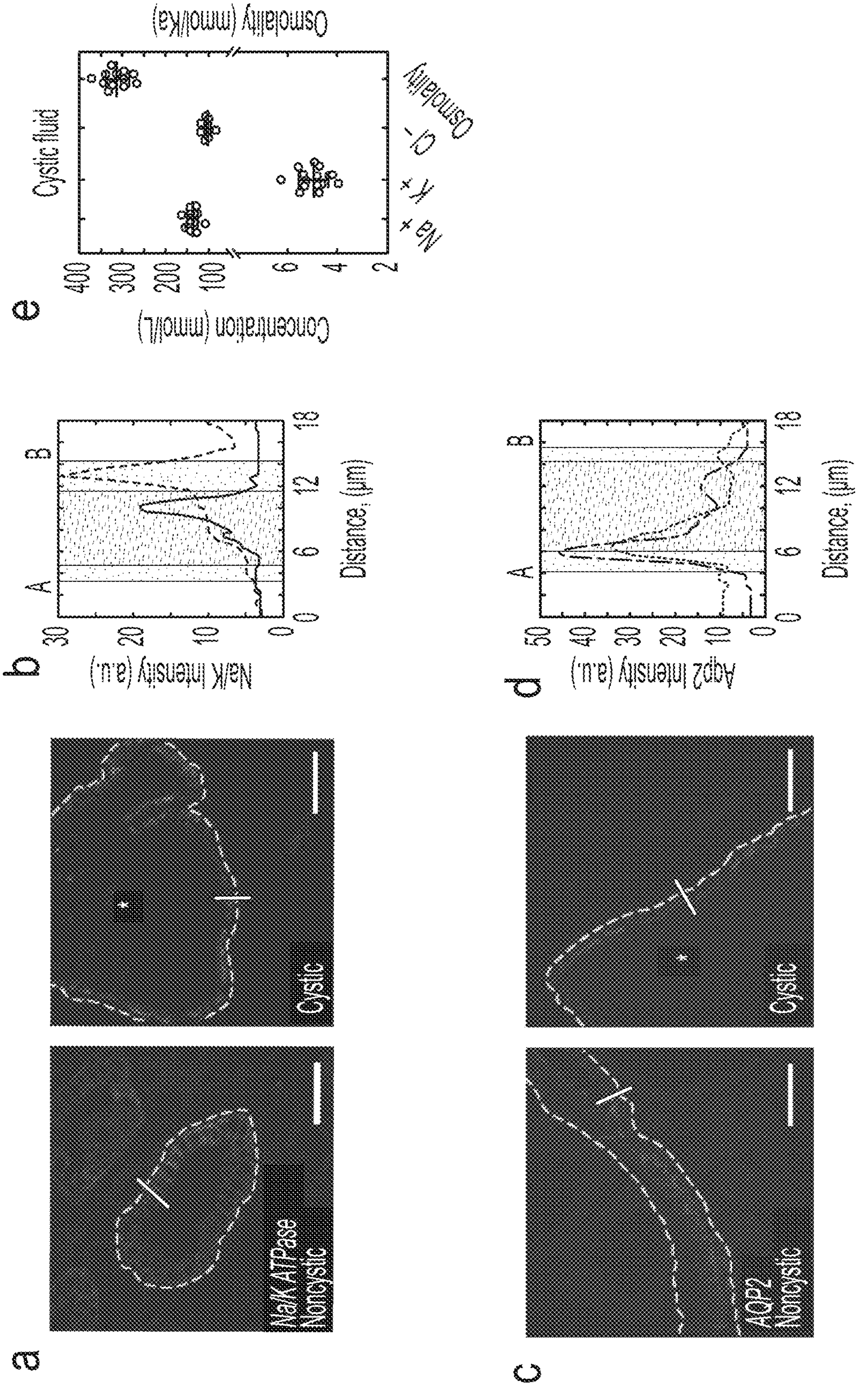
FIGS. 13A-13K are images and graphs showing the phenotypic resemblance of both human renal Wild Type (WT) and ADPKD cystic epithelium grown in an MFKP according to an embodiment of the invention.
Figures 13A, 13B, 13C, 13D, 13E, 13F, 13G, 13H, 13I, 13J, 13K:
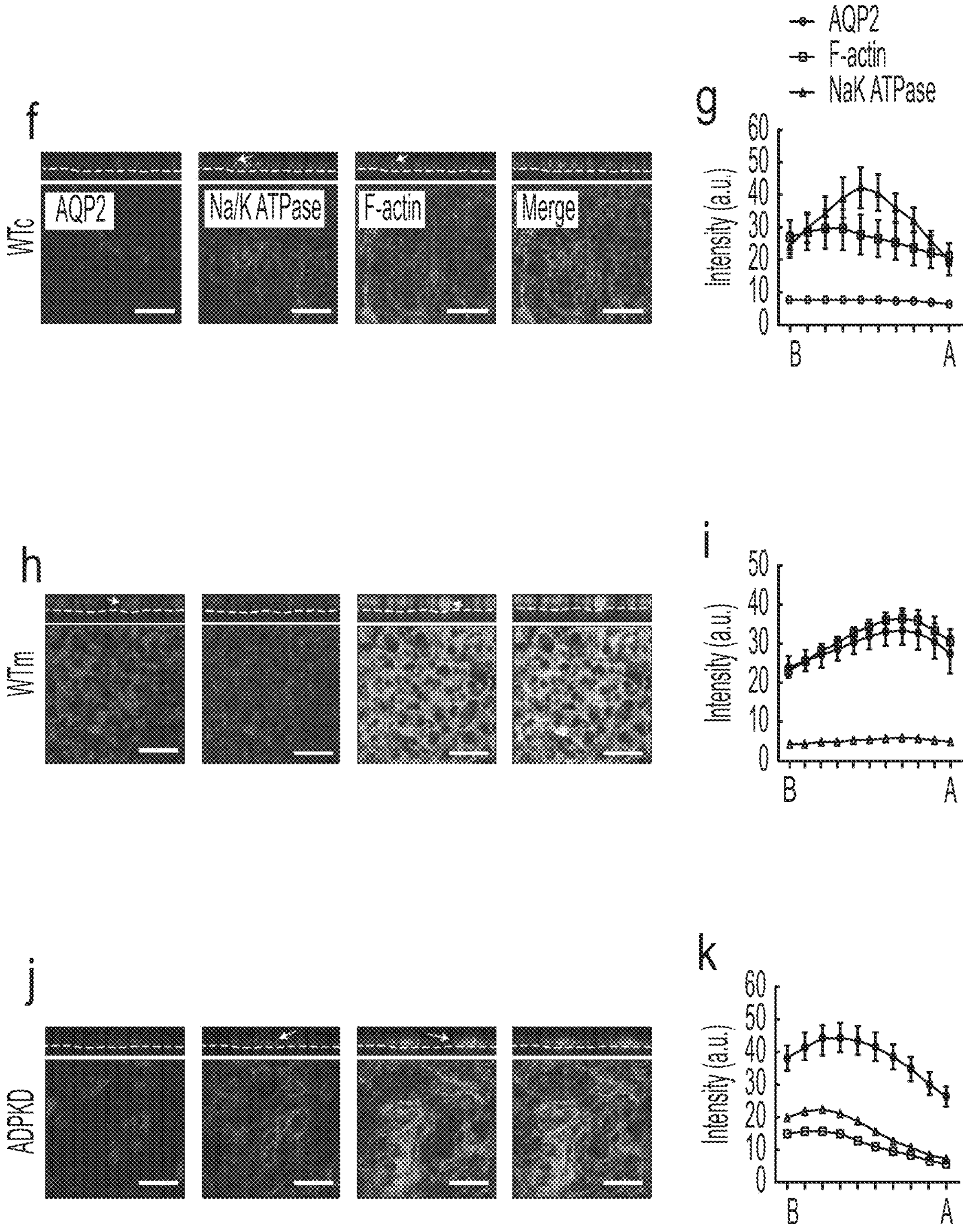

Phenotypic Similarity of Cells in MFKP with Tissue Section Under Normal and Diseased Condition Tissue sections from normal human kidney and cystic human ADPKD kidneys were compared with epithelial monolayers (wild type and ADPKD) grown in MFKP. Immunohistochemical analysis of tissue sections reveal that NKA is expressed on the basolateral side of cells in both normal renal tubules and ADPKD cysts (FIG. 13A, 13B). AQP2 is however enriched on the apical or sometimes sub-apical domains for both normal human kidney and ADPKD cysts (FIG. 13C, 13D). The asterisk indicates the lumen side in cystic tissue section. This indicates that the usual markers of apico-basal polarity are similar in both normal tubular and cystic cells. The normal cells demonstrate regular cuboidal columnar morphology. However, cystic cells have an irregular, stretchy shape and decreased cell height (FIG. 13A, 13C).

The progressive growth of fluid filled cysts leads to increase in total kidney volume, which impairs normal function of the kidney in ADPKD patients [7]. Fluid accumulates into the cyst lumen over long period of time and the hydrostatic pressure is sustained by the epithelium lining the cyst. The fluid collected from the same cysts from which the cells for PPC experiments were extracted and assayed (FIG. 13E). The average osmolality of the fluid collected from all the 16 cysts was 315.83 mmol/kg, and the concentrations of Na+, K+ and Cl— were determined to be 137.19, 4.93 and 100.75 mmol/L, which is in the similar range of normal interstitial fluid [8]. Therefore, even if the cells pump ions and hence water from basal to apical side, the steady state osmolality and ion concentration were similar to interstitial fluid due to water flux into the lumen.

Immunocytochemical analysis of wild type cortex (WTc) grown in MFKP demonstrates co-localization of AQP2, NaKATPase and F-actin. XY image represents top view of the cells on the porous membrane and XZ images show cross-sectional view of the cells along a line of interest (FIG. 13F). The dashed white line in XZ image represents the porous membrane. Quantification of apico-basal intensity for AQP2, NKA and F-actin in WTc epithelium showed enrichment of NKA primarily in the basolateral domain of the cells indicated by white arrow on the corresponding XZ image in FIG. 3C. AQP2 intensity was low indicating absence of the protein in WTc cells, as the cortical tissue primarily is comprised of proximal tubule cells which lack AQP2 (FIG. 13F). F-actin was fibrous on the basal side with strong enrichment in the cell-cell junctions (indicated by arrow in XZ) was observed. F-actin XZ images demonstrate that WTc epithelium exhibit the regular columnar cuboidal epithelium like that of cells in the non-cystic tissue sections (FIG. 13A, 13F). In case of WTm cells, AQP2 was highly enriched in the apical domain and was also present all over the cytoplasm. NKA intensity was low and is primarily located in the basal side of the cells. F-actin was fibrous throughout the cytoplasm and strong enrichment in the cell-cell junctions was observed (marked by arrow in the F-actin XZ image (FIG. 13H, 13I)). ADPKD cells were determined to have AQP2 in on the apical side in a sporadic fashion in the epithelium. NKA was enriched in the baso-lateral domain and is not uniformly distributed all over the epithelium indicating cell type heterogeneity. F-actin was highly fibrous in the baso-lateral domain and unlike normal cells localization in the cell-cell junction was low (FIG. 13J, 13K).

Normal and Diseased Cells on Permeable and Impermeable Substrate

In order to investigate the influence of ΔP on the mRNA expression of the cells, qPCR on ten important genes involved in regulating ion/water transport and mechano-sensation was performed. Heatmaps indicating the expression of mRNAs extracted from WTc, WTm and ADPKD cells grown on permeable substrate (MFKP) and on impermeable substrate (tissue culture treated polystyrene dishes). The rows are normalized such that the relative concentration of across the cells lines has been shown (FIG. 16A). The genes under investigation included Aquaporins (AQP1, AQP3 and AQP5) and ion-pumps (NKA, NHE1, NKCC1, NKCC2) and ion-channels (CFTR, TRPM7 and TRPV4). Except for TRPM7 and TRPV4, the expression for all other genes was higher in cells grown in MFKP as compared to that on impermeable substrate, suggesting that the monolayer becomes much more physiologically relevant when grown in MFKP. Two biological repeats were done for each condition.

Cells plated on the impermeable substrate seemed to express a higher abundance of polycysin protein than cells plated on permeable substrate, when analyzed by western blot. Since equal loading of protein was ensured by use of a loading control (β-actin), it is certain that an equal number of cells is represented in each lane. This leads us to believe that the cells express protein differently on the different substrates. This phenomenon may be explained by the ability of the cells to form polarized layers on the permeable membrane. The cells may be able to continue dividing for longer and therefore require more time to fully express the Polycystins. However, the cells grown on impermeable substrate do not polarize but do become confluent quickly, therefore expression of Polycystins may be higher in these cells. Polycystin levels are generally low in adult kidney cells yet it is possible to detect a weak band in each of the samples by western blot. Both Polycystin 1 and Polycystin 2 appear to be expressed in the ADPKD derived cells. This indicates that the mutation in the ADPKD kidney is not a full deletion of neither PKD1 nor PKD2 but rather appears to affect function. This phenomenon has been noted in animal models where dosage of Polycystins affects cyst growth [9] and loss-of-function of Polycystin 1 is linked to cystic disease [10]. FIG. 16B-16F confirms that one can detect Polycystin expression levels in all samples.

Role of Hydrostatic Pressure Gradient in Localization of NKA in Normal and Diseased Human Primary Cells.

Figures 17A, 17T:
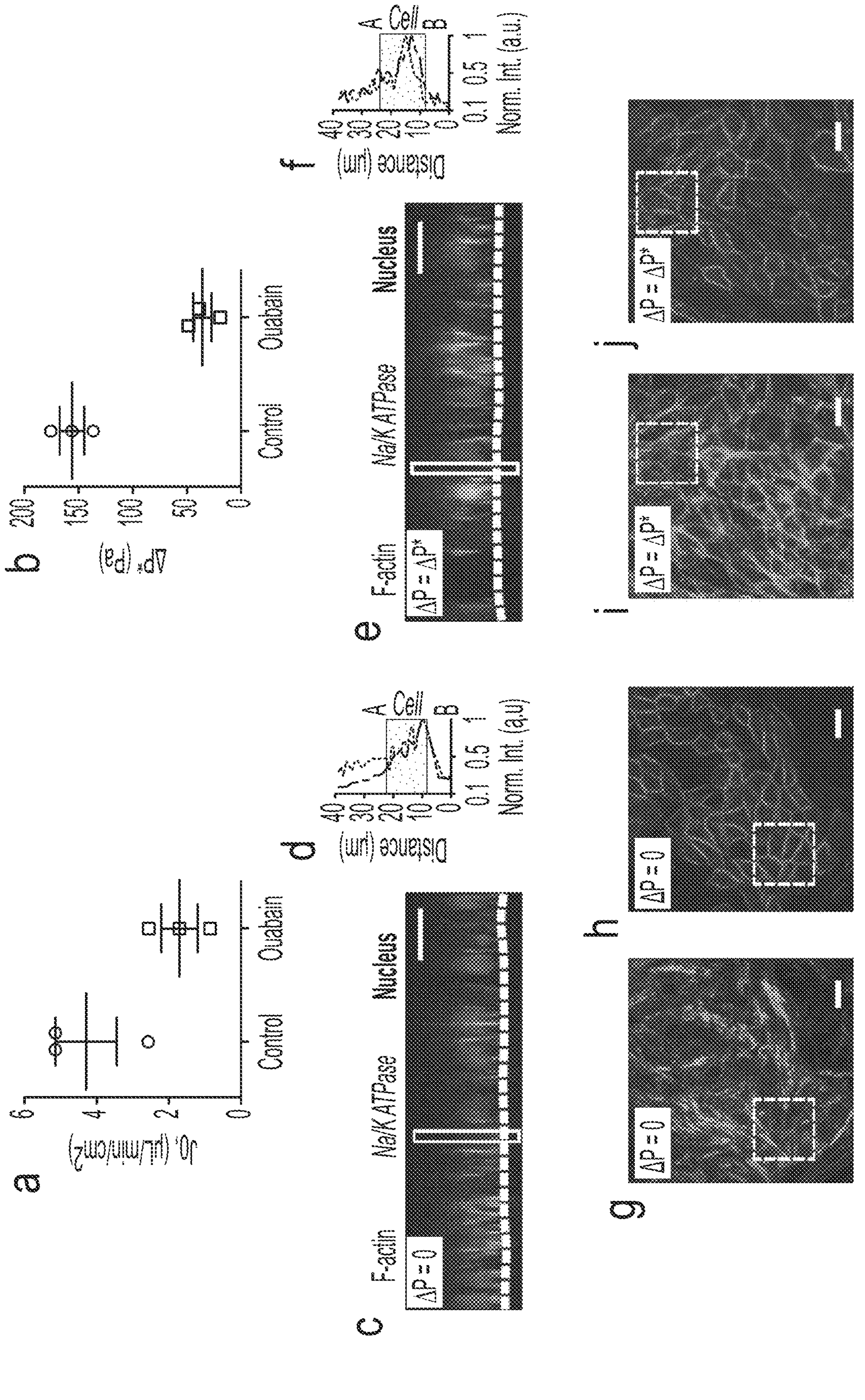
FIGS. 17A-17T are graphs and images showing the role of stall pressure on a specific cell type.
Figures 17A, 17T:
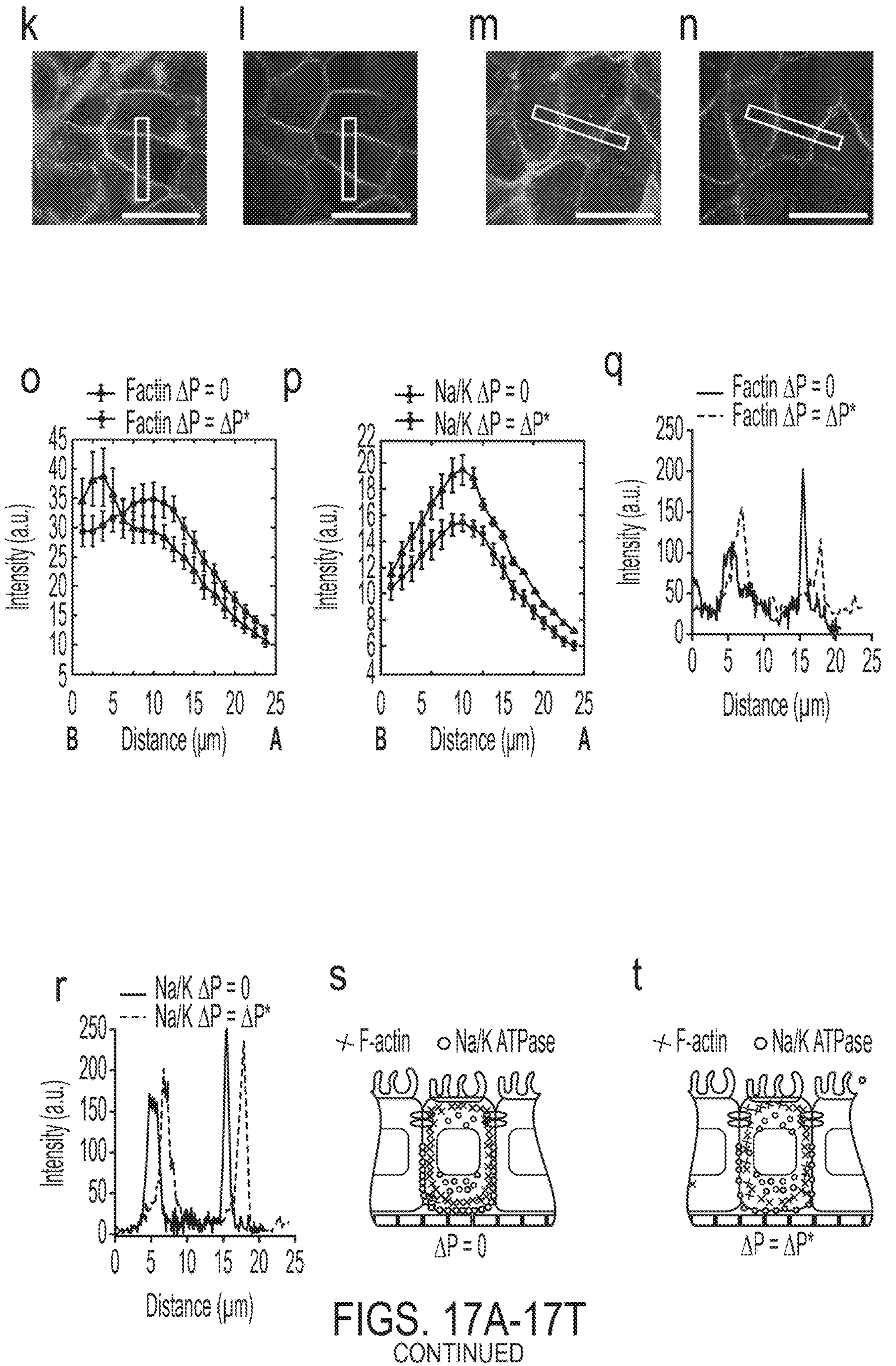
Figures 18A, 18T:
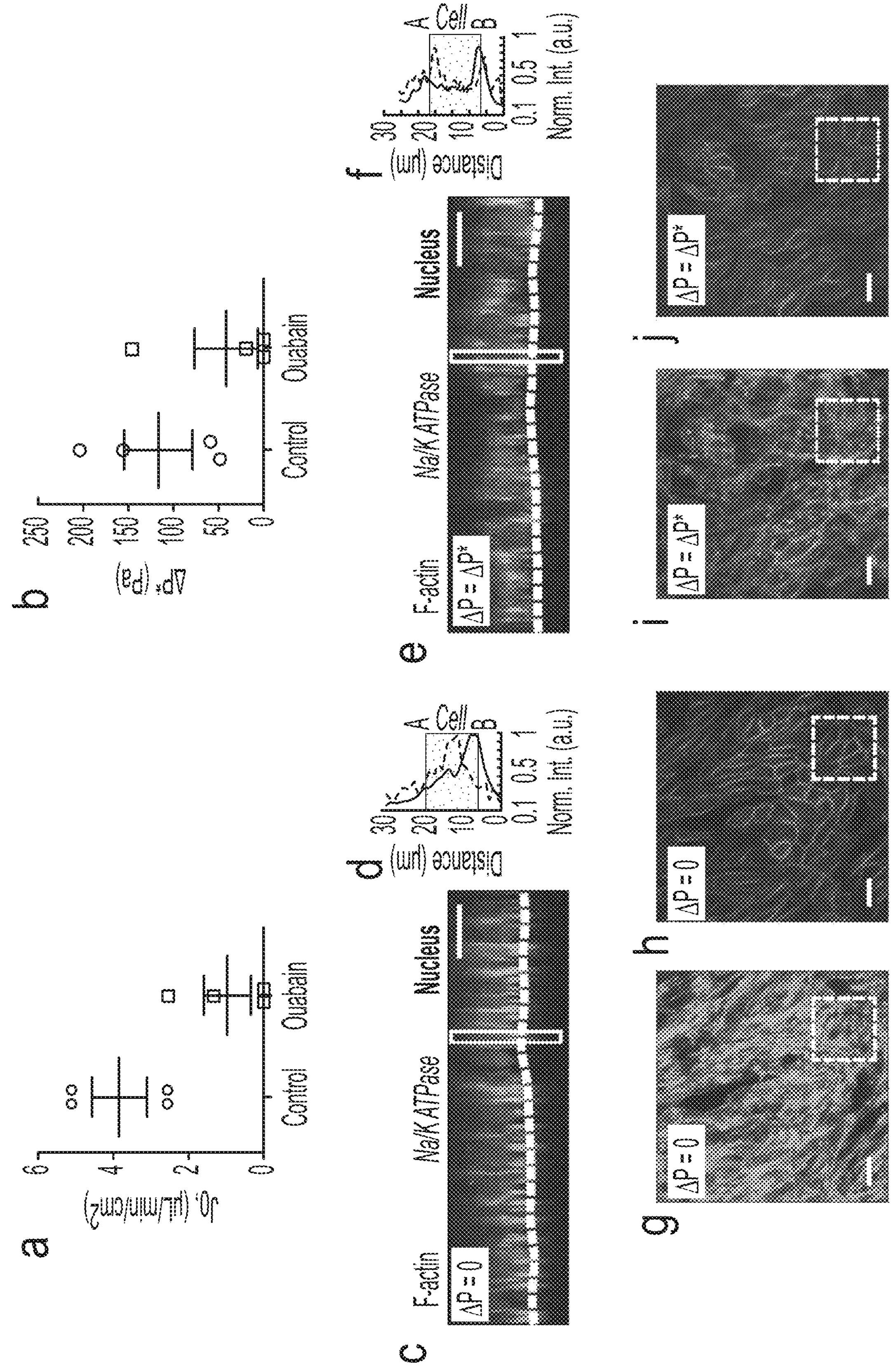
FIGS. 18A-18T are graphs and images showing the role of stall pressure on a specific cell type.
Figures 18A, 18T:
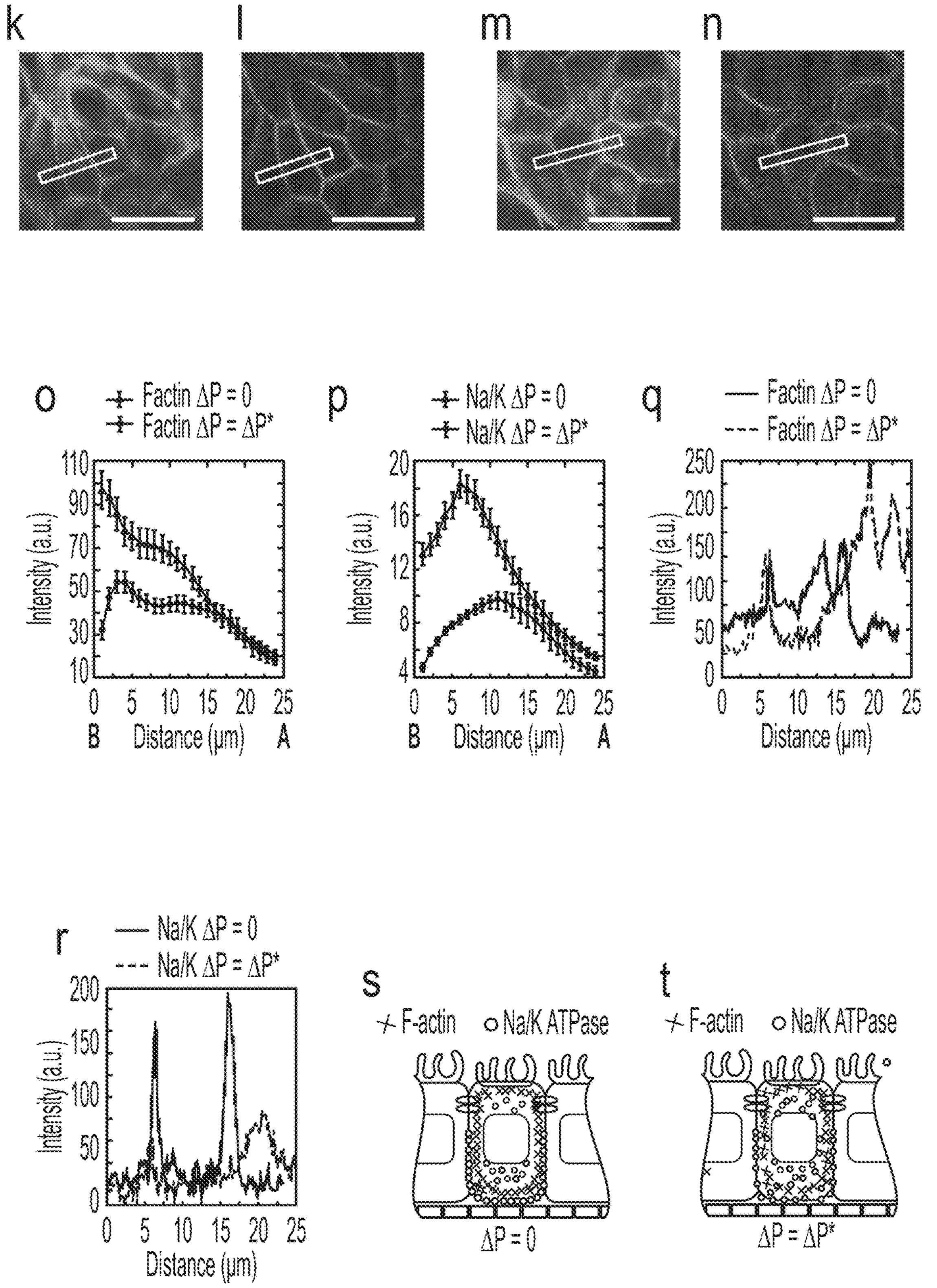
Figures 19A, 19T:
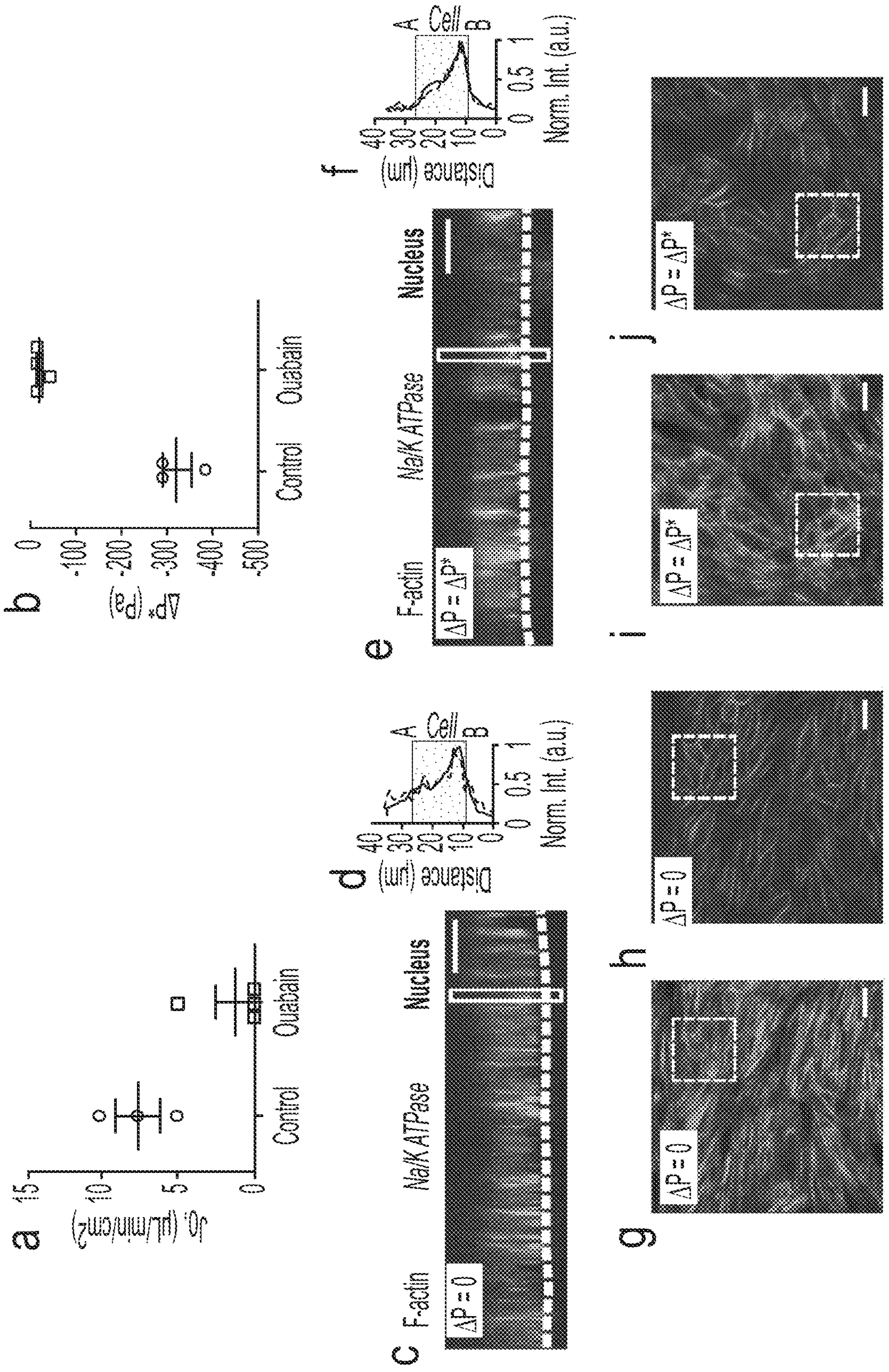
FIGS. 19A-19T are graphs and images showing the role of stall pressure on a specific cell type.
Figures 19A, 19T:
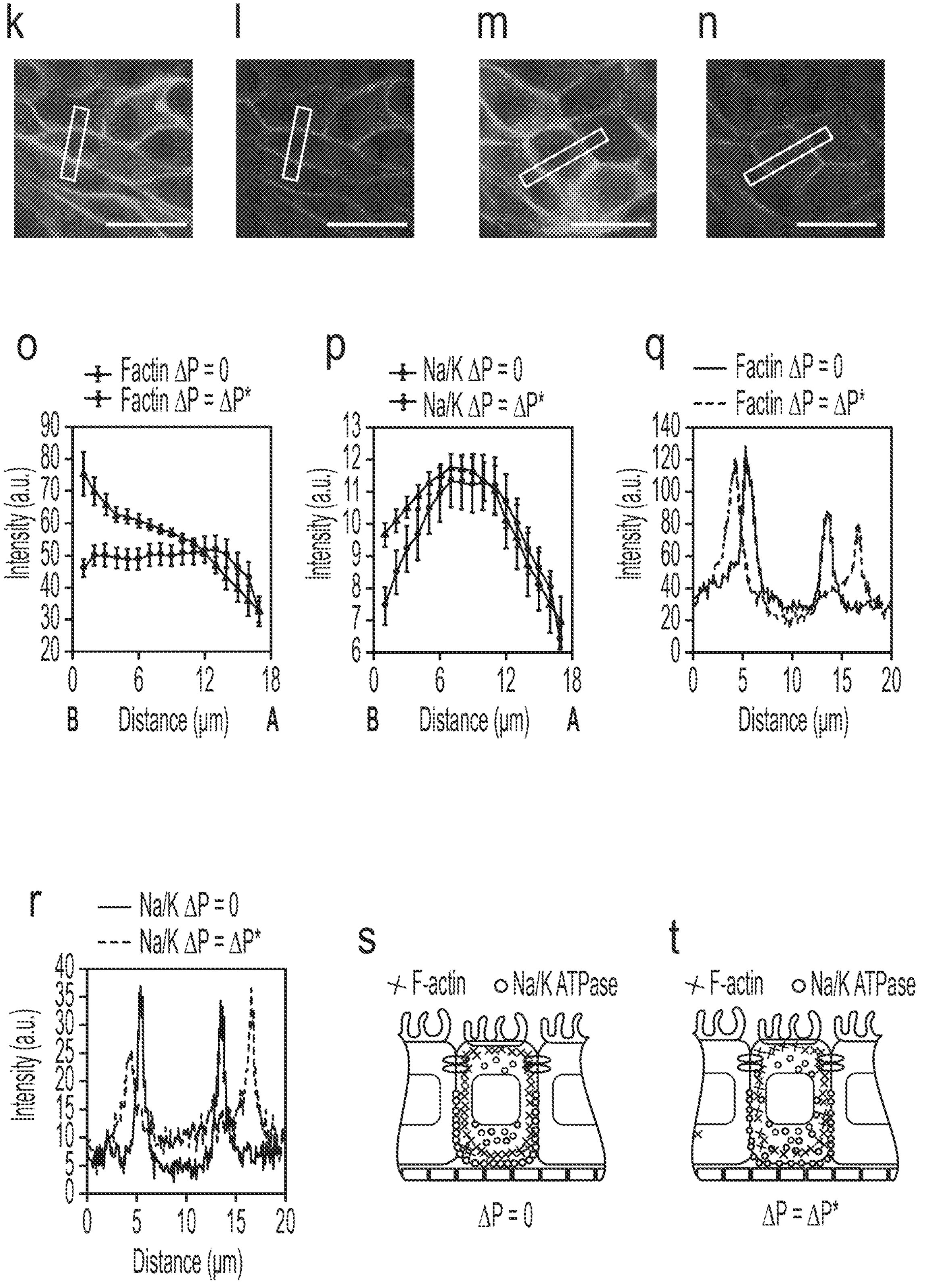

NKA (NKA) has been implicated as the driving force behind trans-epithelial Na+ transport and vectorial fluid movement in both normal and diseased cells [11]. Upon Ouabain induced inhibition of NKA in WTc cells, the equilibrium fluid flux (J0) decreased from 4.3 to 1.7 μL/min/$cm^2$ and stall pressure (ΔP*) decreased from 157 Pa to 34 Pa (FIG. 17A, 17B). For WTm cells, overnight incubation with 274 μM Ouabain caused a decrease of J0 from 4.3 to 1.0·μL/min/cm2 and ΔP* from 56 Pa to 42 (ΔP*) (FIG. 18A, 18B). Ouabain caused a similar decrease in both J0 and ΔP* for ADPKD cells as well (FIG. 19A, 19B). Even though the direction of fluid flow in normal human renal tubular and ADPKD cystic cells are different, J decreased with ΔP for all the three types of primary cells. To investigate the role of ΔP on the localization of NKA, a hydrostatic pressure difference of 200 Pa was applied to the basal channel for WT cells and to the apical channel for ADPKD cells. These cells were then fixed and stained to examine for cytoskeletal organization and NKA localization.

In case of WTc cells in control conditions (indicated by ΔP=0), F-actin is cortical in nature and primarily localized in the basal side, forming thick stress fibers (FIG. 17C, 17D, 17G). NKA is enriched in the canonical baso-lateral domain with strong enrichment on lateral domain (FIG. 17C, 17D, 17H). However, upon application of basal stall pressure (indicated by ΔP=ΔP*), the basal stress fibers disappeared. The F-actin intensity in the cell-cell junctions was thicker in case of stall pressure as compared to control cells, indicating F-actin reinforcement in the junctions with perturbation (FIG. 17K, 17M, 170, 17Q). The baso-lateral polarization and the enrichment of NKA on the lateral side was same under both control and basal ΔP* (FIG. 17K-17R). The total NKA intensity was calculated by randomly choosing 20 cells in the maximum intensity projected view of both control and ΔP* cells (FIG. 17H, 17J). In case of cells exposed to basal ΔP*, The total intensity had a wide distribution as compared to the control cells (FIG. 4D). This could be the reason why the NKA intensity of individual slices decreased a bit in the lateral domain (FIG. 17P). However the difference in the average NKA intensity under both conditions was not significant (p=0:74) This is consistent with the mRNA levels of ATPA1 under both conditions (FIG. 4E).

WTm cells had thick basal F-actin stress fibers at ΔP=0, which is indicative of strong focal adhesion formation. NKA was polarized on the baso-lateral side as expected (FIG. 18C, 18D, 18G, 18H). Stall pressure (indicated by ΔP=ΔP*) on the basal side caused a loss of basal F-actin fibers but the basalto-apical distribution was still maintained. However, ΔP* induced a dramatic depolarization of NKA as the localization changed from baso-lateral to mostly cytoplasmic (FIG. 18E, 18F, 18I, 18J). This effect becomes more clear when the total intensity of each slice in the confocal stack against the distance is plotted (FIG. 180, 18P). Even though the lateral domain has more NKA as compared to the basal side in case of ΔP* but the intensity is lower than that of control cells. As compared to the control, ΔP* also diluted the enrichment of NKA on the lateral side (FIG. 18L, 18N, 18R). The F-actin expression in the cell-cell junctions did not change (FIG. 18K, 18M, 18Q). The loss of F-actin on the basal side in WTm cells due to ΔP* was similar to that of WTc cells but the baso-lateral dilution and depolarization of NKA is more dramatic in WTm cells (FIG. 17S, 17T and 18S, 18T). The total NKA intensity of 20 cells chosen randomly in the maximum intensity projected view of both control and ΔP* cells (FIG. 18H, 18J) was compared. It was determined that the total NKA expression decreased with basal ΔP* (p<0:0001) (FIG. 4*f*). Therefore, for WTm cells, basal ΔP* not only changed the localization of NKA but also decreased the overall expression in the cells, which is consistent with the decrease in mRNA expression of ATPA1 under similar perturbation (FIG. 4G).

Like WTc and WTm cells, cystic cells from ADPKD patients also have thick F-actin stress fibers on the basal side. The intensity of F-actin is more on the basal side as compared to the apical side (FIG. 17C, 17D, 17G, 18C, 18D, 18G and 19C, 19D, 19G). NKA is also polarized in the baso-lateral domain but the total expression is lower than that of WTc and WTm cells (FIG. 19C, 19D, 19H and FIG. 4H). Apical ΔP* changed the F-actin organization but not the NKA expression or localization. Unlike WTc and WTm where basal ΔP* caused a dramatic decrease in basal F-actin stress fibers, in case of ADPKD cells, Apical ΔP* induced a small decrease of basal F-actin stress fibers (FIGS. 17G, 17I, 170, 18G, 18I, 180 and 19G, 19I, 19O). Rather the enrichment of F-actin on the sub-apical domain was observed. Clearly, all three cell types changed their cytoskeletal organization of F-actin when exposed to a hydrostatic pressure difference. NKA localization remained baso-lateral under both conditions (FIG. 19C-19F, 19H, 19J). The total intensity was also same in both conditions (p=0:13) (FIG. 4H). The F-actin enrichment in the cell-cell junction and the NKA enrichment on the lateral side of the cells was also same under both conditions (FIG. 19K-19N, 19Q, 19R).

References from Example 3

[1] Lever, J. E., Inducers of mammalian cell differentiation stimulate dome formation in a differentiated kidney epithelial cell line (MDCK), Proceedings of the National Academy of Sciences 76, 3, 1323-1327, (1979).

[2] Yang, J., Duan, X., Fraser, A., Ewald, A. and Sun, S. X., A microscale pressure sensor based on immiscible fluid/fluid interface. Manuscript submitted for publication, (2019).

[3] Maschmeyer, Ilka, et al. A four-organ-chip for interconnected long-term co-culture of human intestine, liver, skin and kidney equivalents, Lab on a Chip 15.12, 2688-2699, (2015).

[4] Latorre, Ernest, et al. Active superelasticity in three-dimensional epithelia of controlled shape, Nature 563, 7730, 203 (2018).

[5] Weinstein, A. M., A mathematical model of rat proximal tubule and loop of Henle. American Journal of Physiology-Renal Physiology, 308 (10), F1076-F1097, (2015).

[6] Jiang, H. and Sun, S. X. Cellular pressure and volume regulation and implications for cell mechanics. Biophysical Journal. 105, 609-619 (2013).

[7] Grantham, Jared J., Arlene B. Chapman, and Vicente E. Torres. "Volume progression in autosomal dominant polycystic kidney disease: the major factor determining clinical outcomes." Clinical journal of the american society of Nephrology 1.1 (2006): 148-157.

[8] Rohatgi, Rajeev, et al. "Cyst fluid composition in human autosomal recessive polycystic kidney disease." Pediatric Nephrology 20.4 (2005): 552-553.

[9] Hopp, Katharina, et al. Functional polycystin-1 dosage governs autosomal dominant polycystic kidney disease severity, The Journal of clinical investigation 122.11, 4257-4273, (2012).

[10] Brasier, J. L., Henske, E. P. Loss of the polycystic kidney disease (PKD1) region of chromosome 16p13 in renal cyst cells supports a loss-of-function model for cyst pathogenesis. The Journal of clinical investigation, 99 (2), 194-199 (1997).

[11] Terryn, Sara, et al., Fluid transport and cystogenesis in autosomal dominant polycystic kidney disease. Biochimica et Biophysica Acta (BBA)-Molecular Basis of Disease 1812.10, 1314-1321, (2011).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A microfluidic device for measuring a fluidic flux through a tissue layer, comprising:

a first micro-patterned layer;

a second micro-patterned layer attached to the first micro-patterned layer;

a porous membrane disposed between the first micro-patterned layer and the second micro-patterned layer, wherein the second micro-patterned layer and the porous membrane together define an upper channel across an upper surface of the tissue layer while in use;

wherein the first micro-patterned layer and the porous membrane together define a lower channel across a lower surface of the tissue layer while in use;

a pressure monitor arranged in operative communication with the upper channel and the lower channel, the pressure monitor configured to measure a fluidic pressure in the upper channel and a fluidic pressure in the lower channel; and a fluidic flux monitor arranged in operative communication with the upper channel and the lower channel, the fluidic flux monitor being configured to provide a measurement of said fluidic flux, wherein the fluidic flux monitor comprises a microcapillary configured to measure both (i) transepithelial fluid flux and (ii) hydraulic pressure in the microfluidic device, and wherein said fluidic flux is measured as a function of said fluid pressure to determine a state of said tissue layer.

2. The microfluidic device of claim 1, wherein at least one of the first and second micro-patterned layers further comprises a base layer attached to at least one of the first and second micro-patterned layers.

3. The microfluidic device of claim 1, wherein the porous membrane has a thickness less than or equal to 50 micrometers.

4. The microfluidic device of claim 1, wherein the porous membrane comprises a plurality of pores that have sizes sufficiently small such that cells within the tissue layer will not pass therethrough.

5. The microfluidic device of claim 1, wherein the porous membrane comprises a plurality of pores that have an ensemble average diameter of between about 1 micrometer to about 10 micrometers.

6. The microfluidic device of claim 1, further comprising an extracellular matrix protein coating on at least one side of the porous membrane.

7. The microfluidic device of claim 1, wherein the upper channel and the lower channel are each sufficiently narrow in a cross-sectional dimension such that the upper channel and the lower channel each support laminar flow.

8. The microfluidic device of claim 1, wherein the pressure monitor and a fluidic flux monitor are a single unit.

9. The microfluidic device of claim 1, wherein the microcapillary is fluidly coupled to a port of the microfluidic device that is in fluid communication with one of the upper channel or the lower channel.

10. The microfluidic device of claim 9, wherein an optical detection system monitors a height of fluid in the microcapillary, wherein the fluidic pressure is determined from the height of the fluid, and the fluidic flux is determined from a change in the height over time.

11. A system for measuring a fluidic flux across a tissue layer comprising a microfluidic device, the microfluidic device comprising:

a first micro-patterned layer;

a second micro-patterned layer attached to the first micro-patterned layer;

a porous membrane disposed between the first micro-patterned layer and the second micro-patterned layer, wherein the second micro-patterned layer and the porous membrane together define an upper channel across an upper surface of the tissue layer while in use;

wherein the first micro-patterned layer and the porous membrane together define a lower channel across a lower surface of the tissue layer while in use; and a pressure monitor arranged in operative communication with the upper channel and the lower channel, wherein the pressure monitor is configured to measure a fluidic pressure in the upper channel and a fluidic pressure in the lower channel; and a fluidic flux monitor arranged in operative communication with the upper channel and the lower channel, the fluidic flux monitor being configured to provide a measurement of said fluidic flux, wherein the fluidic flux monitor comprises a microcapillary configured to measure both (i) trans-epithelial fluid flux and (ii) hydraulic pressure in the microfluidic device, and wherein said fluidic flux is measured as a function of said fluid pressure to determine a state of said tissue layer.

12. The system of claim 11, wherein the fluidic flux monitor in operative communication with at least one of said upper channel and said lower channel is configured to measure the fluidic flux from at least one of said lower surface or said upper surface of said tissue layer to provide a measure of said fluidic flux through said tissue layer, and wherein said tissue layer is a continuous layer without gaps such that portions of a fluid flowed across said upper surface of said tissue layer only pass through said porous membrane by passing through cells of said tissue layer.

* * * * *